US006977157B2

(12) United States Patent
Takasugi et al.

(10) Patent No.: US 6,977,157 B2
(45) Date of Patent: Dec. 20, 2005

(54) CLOCK GENE PROMOTER

(75) Inventors: Tomohiro Takasugi, Tsukuba (JP); Wenbin Chen, Tsukuba (JP); Seiichi Hashimoto, Tsukuba (JP)

(73) Assignee: Astellas Pharma Inc., Tokyo ( * ) Notice: Subject to any disclaimer, the term of this patent is extended or adjusted under 35 U.S.C. 154(b) by 55 days.

(21) Appl. No.: 10/415,489

(22) PCT Filed: Apr. 2, 2002

(86) PCT No.: PCT/JP02/03290

§ 371 (c)(1),
(2), (4) Date: Apr. 30, 2003

(87) PCT Pub. No.: WO02/081682

PCT Pub. Date: Oct. 17, 2002

(65) Prior Publication Data

US 2004/0137443 A1 Jul. 15, 2004

(30) Foreign Application Priority Data

Apr. 5, 2001 (JP) ....................................... 2001-107467
Jun. 18, 2001 (JP) ....................................... 2001-183087
Dec. 17, 2001 (JP) ....................................... 2001-383743

(51) Int. Cl.[7] .......................... C12Q 1/02; C07H 21/04; C12N 5/00; A01K 67/027; G01N 33/00

(52) U.S. Cl. ........................ 435/29; 435/325; 536/24.1; 536/23.1; 800/3; 800/14; 800/18

(58) Field of Search ........................ 435/6, 69.1, 320.1, 435/325, 29; 800/8, 18, 3, 14; 536/23.1, 24.1

(56) References Cited

U.S. PATENT DOCUMENTS 6,475,744 B1 * 11/2002 Reppert et al. .............. 435/7.1

FOREIGN PATENT DOCUMENTS

WO WO 01/07654 A1 2/2001
WO WO 01/36618 A2 5/2001

OTHER PUBLICATIONS

Yamazaki et al. Resetting central and peripheral circadian oscillators in transgenic rats. Science. vol. 288, pp. 682–685, Apr. 2000.*

Wall. Transgenic livestock: Progress and prospects for the future. Theriogenology. vol. 45, No. 1, pp. 57–68, 1996.*

Apostel et al. Reduced expression and Increased CpG dinucleotide methylation of the rat APOBEC–1 promoter in transgenic rabbits. Biochemica et Biophysica Acta. vol. 1577, pp. 384–394, 2002.*

Cowan et al. Targeting gene expression to endothelium in transgenic animals: A comparison of the human ICAM–2, PECAM–1 and endoglin promoters. Xenotransplantation, vol. 10, pp. 223–231, 2003.*

Cameron, Recent advances in transgenic technology. Molecular Biotechnology. vol. 7, pp. 253–265, 1997.*

Shin Yamazaki et al. "Resetting Central and Peripheral Circadian Oscillators in Transgenic Rats" vol. 288 SCIENCE (2000) pp. 682–685.

Shun Yamaguchi et al. "View of a mouse clock gene ticking" vol. 409 NATURE (2001) p. 684.

Akira Shimamoto et al. "Cap Site cDNA[tms] no Kaihatsu to Yuyosei" vol. 66 WAKO Junyaku Jiho (1998) pp. 10–13.

Urs Albrecht et al. "A Different Response of Two Putative Mammalian Circadian Regulators, mper1 and mper2, to Light" vol. 91 CELL (1997) pp. 1055–1064.

Database EMBL 'Online!,'"Mus musculus chromosome 1 clone RP23–29D20 map 1," Feb. 5, 2002, XP002336771.

Database EMBL 'Online!, "Homo sapiens BAC clone RP11–5024 from 2, complete sequence," October 29, 1999, XP002336772.

S. Yamaguchi, et al., "The 5'upstream region of mPerl gene contains two promoters and its responsible for circadian oscillation," *Current Biology*, vol. 10, No. 14, Jul. 13, 2000, pp. 873–876, XP002336767.

Xiaowei Jin et al., "A molecular mechanism regulating rhythmic output from the suprachiasmatic circadian clock," *Cell*, vol. 96, No. 1, Jan. 8, 1999, pp. 57–68, XP002336768.

* cited by examiner

*Primary Examiner*—Terry McKelvey
*Assistant Examiner*—Jennifer Dunston
(74) *Attorney, Agent, or Firm*—Sughrue Mion, PLLC

(57) ABSTRACT

The present invention discloses a Period2 gene promoter, a construct containing the promoter and a reporter gene, a cell containing the construct, a transgenic animal harboring the construct, and a method for screening a substance which controls expression or oscillatory expression of a biological clock gene. The screening method uses the above cell, a suprachiasmatic nucleus section or peripheral tissue of the above transgenic animal or the above transgenic animal.

12 Claims, 8 Drawing Sheets

CLOCK GENE PROMOTER

TECHNICAL FIELD

The present invention relates to a biological clock gene promoter, a construct containing the promoter and a reporter gene, a cell containing the construct, a transgenic animal harboring the construct, and a method for screening a substance which controls expression and/or oscillatory expression of a biological clock gene.

BACKGROUND OF THE INVENTION

It is known that a large number of organisms are possessed of a mechanism in their bodies, which generates circadian rhythm with ablout 24 hour cycle (Reference 1). In mammals, the mechanism generating circadian rhythm controls sleep-wake rhythm, blood pressure, body temperature and a part of hormone secretion rhythm (Reference 2, Reference 3). As diseases caused by the circadian rhythm disturbance, sleep-wake rhythm disorder (delayed sleep phase syndrome (DSPS), non-24 hour sleep-wake syndrome), seasonal depression, jet lag syndrome (JET-LAG), sleep disturbance in night and day shift workers, nocturnal poriomania and delirium found in patients with senile dementia and the like have been reported (References 4 to 7). In addition, there is a report stating that a part of children with school refusal or workers with refusal to attend firm as a social problem is caused by a circadian rhythm disorder (Reference 8). Increase in the number of patients with rhythm disorder is expected in the future by the increase in advanced aged and the progress of globalization of social structure, but it is the present situation that a secure rhythm disorder improving agent is not present. On the other hand, there are reports stating that bright light therapy, including staring at a light of about 5,000 luxes continuously for several hours in the early morning, shows excellent therapeutic effect on nocturnal poriomania and delirium in patients with senile dementia, rhythm disturbance in patients with delayed sleep phase syndrome (DSPS) or the like (References 6, 7 and 9 to 12). However, since the bright light therapy which requires looking at a high lux light source for a prolonged period of time is painful or burden for patients and their caretakers, agents as substitutes for this light therapy are highly expected.

Based on tissue destruction and tissue transplantation experiments, it has been found in 1972 that the rhythm center of mammals is present in suprachiasmatic nucleus (SCN) (References 13 and 14). However, molecular mechanism of the rhythm generation has been unclear until recent years (Reference 15). On the other hand, an arrhythmic mutant (Period mutant) of *Drosophila melanogaster* has been prepared by a genetic technique and then a Period gene of *Drosophila melanogaster* has been cloned (Reference 16, Reference 17). Since oscillatory expression of Period gene with about 24 hour cycle is achieved in *Drosophila melanogaster* through the migration of translated Period protein (PERIOD) into the nucleus and subsequent inhibition of its own transcription (negative feedback mechanism), it is considered that outputs of circadian rhythm (behavior, timing of eclosion) are finally developed by this (References 18 and 19). In mammals, on the other hand, human and mouse Period1 gene (Period1; Per1) has been cloned in 1997 as a homologue of the *Drosophila* Period gene (Reference 20, Reference 21). Thereafter, mouse Period2 gene (Period2; Per2) (References 22 and 23) and mouse Period3 gene (Period3; Per3) (References 24 and 25) have been cloned. In addition to these, mouse Clock gene (Clock) (Reference 26) and mouse Bmal1 gene (Bmal1) (Reference 27) have been reported as mammalian clock genes. Thus, it is possible for now to understand the rhythm generation mechanism at the molecular level. Actually, it has been found that the Clock gene and Bmal1 gene are important for the circadian oscillation of a clock gene (References 44 and 45) and that a protein encoded by the Clock gene and a protein encoded by the Bmal1 gene bind to a CACGTG type E-box and activate transcription of said clock gene, namely, the CACGTG type E-box sequence is essential for the transcriptional activation by the CLOCK and BMAL1 (Reference 27).

A transgenic rat (mPer1; luc transgenic rat) harboring a DNA prepared by ligating an upstream sequence of a mouse clock gene, Period1 gene (mPer 1), with a luciferase gene has been reported in 2000 (Reference 28). It has been reported that the Period1 shows oscillatory expressions in not only the suprachiasmatic nucleus but also in peripheral tissues of the living body by measuring the luciferase activity in real time using a photomultiplier tube detector (Photomal) (Reference 28). In addition, similar results have been reported also on a transgenic mouse (mPer1; luc transgenic mouse) harboring a DNA prepared by ligating an upstream sequence of the Period1 gene with a luciferase gene (Reference 43).

It has been suggested that the Period2 gene among the three Period gene homologues takes an important role in the rhythm generation, because its circadian rhythm disappears in mutant mice with artificial gene mutation (Reference 29). Also, it has been reported that the cause of a familial advanced sleep phase syndrome (ASPS) is a point mutation of the Period2 gene (Reference 30). Thus, the Period2 gene is a gene which not only shows abnormal rhythm in the mutant mice but also relates to rhythm disorders in human has been confirmed.

Only the one report regarding the upstream region of Period2 gene is WO 01/07654 on a mouse sequence, and said international publication describes a DNA sequence by defining it as a sequence which controls mouse Period2 transcription and describes about a method for identifying a Period2 transcription inhibitor, which comprises supplying a cell containing sequence (which controls Per2 transcription)-linked reporter gene, introducing a test compound and assaying transcription of the reporter gene. However, there is no specific example on actually obtaining the above DNA sequence described as a sequence which controls mouse Period2 transcription, and there is no description such that it can be obtained. Also, there is no specific example on the determination of transcription start site or measurement of transcriptional activity, too. In addition, there are positions in the disclosed DNA sequence where bases cannot be specified, and sequence information regarding upstream sequence of the Period2 gene is not specifically disclosed.

Also, there are many reports on the analysis of the upstream sequence of Period1 gene, but since Period1 and Period2 genes are located in different chromosomes and have no characteristic common sequence, it did not become information for deducing the Period2 promoter sequence.

Great concern has been directed toward the development of a tool for the screening of useful substances as rhythm disorder improving agents having a mechanism of function to control expression of biological clock genes and a method for screening substances capable of controlling expression of biological clock genes.

DISCLOSURE OF THE INVENTION

As a result of intensive studies, the present inventors have determined for the first time a human Period2 gene promoter sequence as a region which controls transcriptional activity of the human Period2 gene and also as a region that contributes to the oscillatory expression, thereby obtaining a construct containing the above promoter and a reporter gene and a cell containing the above construct. Also, a construct containing the above promoter and a reporter gene and a cell containing the above construct were obtained by determining a mouse Period2 gene promoter sequence. In addition, a transgenic animal harboring the above construct was prepared. Next, in spite of the absence of the CACGTG type E-box sequence in the mouse-derived Period2 promoter of the present invention, transcriptional activation of the Period2 gene by a heterodimer (BMAL1/CLOCK heterodimer) consisting of a protein encoded by a mouse Bmal1 gene and a protein encoded by a mouse Clock gene and oscillatory expression were unexpectedly found. Also, a system by which promoter activity of this gene can be easily detected was constructed. As a result, the present invention provides a Period2 gene promoter, a construct containing the above promoter and a reporter gene, a cell containing the above construct and a transgenic animal harboring the above construct, as tools useful for screening rhythm disorder improving agents as substances which control expression and/or oscillatory expression of biological clock genes, and also provides a convenient method for screening rhythm disorder improving agents, and thus, the present invention has been completed. Also, the term "construct" as used herein means a construct consisting of a DNA constructed by a combination of DNAs such that it shows the function of interest.

The CACGTG type E-box sequence is present in five positions of the upstream of the first exon of the mouse Period1 gene as one of the Period gene homologues, and the region which contributes to the basal activity of Per1 transcription is present in a region containing first exon, its environs and a human-mouse conserved segment of the first intron, but it does not contain these five CACGTG type E-box sequences. The BMAL1/CLOCK heterodimer activates transcription of the mouse Period1 gene by binding to the CACGTG type E-box sequence, but it hardly enhance the transcriptional activity derived from the region which contributes a basal transcriptional activity and contains no CACGTG type E-box sequence (Reference 27). Also, when the five CACGTG type E-boxes of the mouse Period1 gene were mutated, the transcriptional activity in the presence of the BMAL1/CLOCK heterodimer becomes a similar level of the basal transcriptional activity (Reference 34). Based on these facts, it is considered that the BMAL1/CLOCK heterodimer induces transcriptional activation of the mouse Period1 gene via the CACGTG type E-box. On the other hand, it has been reported that the circadian oscillation of Period1 and Period2 genes disappear under constant dark condition in Bmal1 knockout mice (reference 44), and it has been reported that the circadian oscillation of Period1 and Period2 genes attenuate under constant dark condition in Clock/Clock mutant mice (reference 45). That is, it has been found that the Bmal1 and Clock are important for the oscillations. When considered from these results, the DNA sequence defined as sequence, which controls mouse Period2 transcription, in the above WO/01/07654 (that is, it corresponds to a part (from positions 6,050 to 7,761) of a sequence consisting of nucleotides of positions 4,415 to 7,931 in the nucleotide sequence represented by SEQ ID NO:1 which is the DNA nucleotide sequence of the present invention, but is a sequence having inconsistent sequences in several positions) merely indicates a region having basal transcriptional activity because it does not contain the CACGTG type E-box. In the same manner, it was not considered that the DNA derived from Period2 gene of the present invention which does not contain the CACGTG type E-box will show transcriptional enhancement by a BMAL1/CLOCK heterodimer, and its contribution to the oscillatory expression could not be expected, too. However, it was unexpectedly found that the DNA of the present invention which does not contain the CACGTG type E-box shows transcriptional enhancement by a BMAL1/CLOCK heterodimer and also contributes to the oscillatory expression, namely that it is a region important for the oscillatory expression, so that a convenient system for measuring the oscillatory expression was constructed. Namely, since the Period2 promoter of the present invention showed higher activity than that of the mouse Period2 gene sequence containing the CACGTG type E-box (namely, pCH1 of this specification), it was able to construct a more easily detectable system by using the DNA of the present invention and to provide a method for obtaining more useful rhythm improving agents. Thus, the present invention has been accomplished.

Accordingly, the present invention relates to

[1] A DNA which maintains a basal promoter activity and has a promoter activity transcriptionally-activated by a BMAL1/CLOCK heterodimer, which comprises the nucleotide sequence described in the following (a), (b), (c), (d) or (e):

(a) a sequence consisting of nucleotides at positions 7,463 to 7,931 in the nucleotide sequence represented by SEQ ID NO:1, (b) a sequence consisting of nucleotides at positions 6,417 to 7,931 in the nucleotide sequence represented by SEQ ID NO:1, (c) a sequence consisting of nucleotides at positions 5,249 to 7,931 in the nucleotide sequence represented by SEQ ID NO:1, (d) a sequence consisting of nucleotides at positions 4,415 to 7,931 in the nucleotide sequence represented by SEQ ID NO:1, and (e) a sequence consisting of nucleotides at positions 3,820 to 6,068 in the nucleotide sequence represented by SEQ ID NO:2.

[2] A DNA which consists of the nucleotide sequence described in the (a), (b), (c), (d) or (e) according to [1].

[3] A construct which comprises the DNA according to [1] or [2] and a reporter gene.

[4] A cell which comprises the construct according to [3].

[5] A method for screening a substance which controls expression of Period2 gene, comprising the steps of:

allowing the cell according to [4] to contact with a substance to be tested, and measuring a reporter activity.

[6] An transgenic animal transfected with the construct according to [3].

[7] The transgenic animal according to [6], wherein the animal is a rat.

[8] A method for screening a substance which controls expression and/or oscillatory expression of Period2 gene, comprising the steps of:

allowing the cell according to [4] or a suprachiasmatic nucleus section or peripheral tissue of the transgenic animal according to [6] or [7] to react with a substance to be tested, and measuring oscillatory expression.

[9] A method for screening a substance which controls expression and/or oscillatory expression of Period2 gene, comprising the steps of:

administering a substance to be tested to the transgenic animal according to [6] or [7], and measuring oscillatory expression of suprachiasmatic nucleus of the animal.

[10] The screening method according to any one of [5], [8] and [9], wherein the substance which controls expression and/or oscillatory expression of Period2 gene is a substance for improvement of rhythm disorders.

BEST MODE FOR CARRYING OUT THE INVENTION

Figure 1:
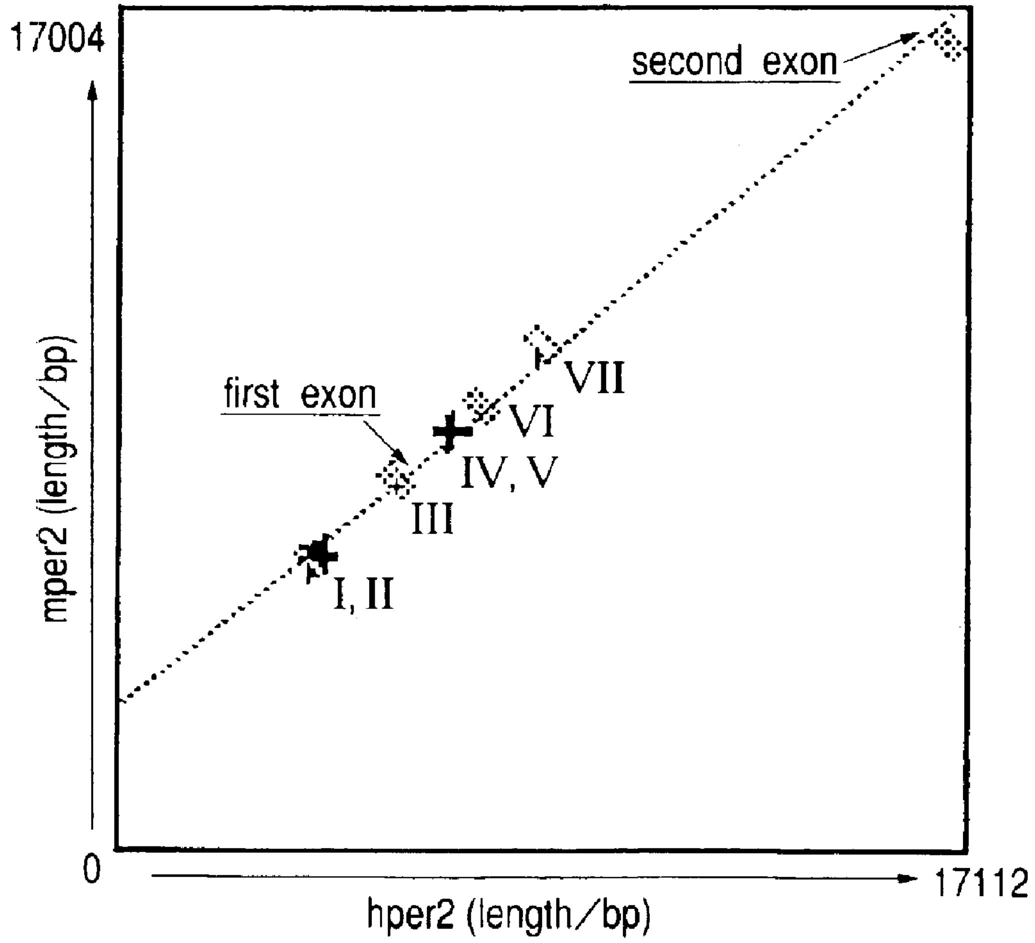
FIG. 1 shows a result of the sequence comparison between upstream regions of mouse Period2 gene and human Period2 gene (hPer 2).

The present invention is explained below in detail.

[DNA of the Present Invention]

The DNA of the present invention contains (a) a sequence consisting of nucleotides at positions 7,463 to 7,931 in the nucleotide sequence represented by SEQ ID NO:1, (b) a sequence consisting of nucleotides at positions 6,417 to 7,931 in the nucleotide sequence represented by SEQ ID NO:1, (c) a sequence consisting of nucleotides at positions 5,429 to 7,931 in the nucleotide sequence represented by SEQ ID NO:1, (d) a sequence consisting of nucleotides at positions 4,415 to 7,931 in the nucleotide sequence represented by SEQ ID NO:1, or (e) a sequence consisting of nucleotides at positions 3,820 to 6,068 in the nucleotide sequence represented by SEQ ID NO:2, and shows a Period2 gene promoter activity.

The term "Period2 gene promoter activity" as used herein means a promoter activity which maintains at least a basal promoter activity as a DNA consisting of a sequence consisting of nucleotides at positions 4,415 to 7,931 in the nucleotide sequence represented by SEQ ID NO:1 (that is, having at least 50% of the activity of the basal promoter activity of a DNA consisting of a sequence consisting of nucleotides at positions 4,415 to 7,931 in the nucleotide sequence represented by SEQ ID NO:1, preferably having substantially the same level of basal promoter activity of the DNA or superior to that) and is also enhanced by BMAL1/CLOCK heterodimer on transcriptional activity (namely to contribute to oscillatory expression).

The term "basal promoter activity" as used herein means a promoter activity when a predetermined period of time (e.g., 48 hours) is passed under no stimulus condition, and the term "no stimulus condition" means specifically conditions in the absence of a BMAL1/CLOCK heterodimer as shown in Example 3. Also, the above "BMAL1/CLOCK heterodimer" is transcription factors which controls each transcription of the Period1 gene, Period2 gene and Period3 gene.

Although the method for judging whether or not a certain DNA shows "Period2 gene promoter activity" is not particularly limited, it can be judged, for example, by verifying that it is substantially the same as or superior to the promoter activity of the DNA consisting of a sequence consisting of nucleotides at positions 4,415 to 7,931 in the nucleotide sequence represented by SEQ ID NO:1, through the measurement of basal promoter activity in the absence of the BMAL1/CLOCK heterodimer as shown in Example 3, and further verifying whether or not it shows dose-dependent transcriptional activation by a BMAL1/CLOCK heterodimer.

The desirable DNA of the present invention includes a DNA consisting of a sequence consisting of nucleotides at positions 7,463 to 7,931 in the nucleotide sequence represented by SEQ ID NO:1, a sequence consisting of nucleotides at positions 6,417 to 7,931 in the nucleotide sequence represented by SEQ ID NO:1, a sequence consisting of nucleotides at positions 5,429 to 7,931 in the nucleotide sequence represented by SEQ ID NO:1 or a sequence consisting of nucleotides at positions 4,415 to 7,931 in the nucleotide sequence represented by SEQ ID NO:1, or a DNA consisting of a sequence consisting of nucleotides at positions 3,820 to 6,068 in the nucleotide sequence represented by SEQ ID NO:2. However, any DNA is included in the DNA of the present invention, so long as the DNA contains a DNA consisting of a sequence consisting of nucleotides at positions 7,463 to 7,931 in the nucleotide sequence represented by SEQ ID NO:1, a sequence consisting of nucleotides at positions 6,417 to 7,931 in the nucleotide sequence represented by SEQ ID NO:1, a sequence consisting of nucleotides at positions 5,429 to 7,931 in the nucleotide sequence represented by SEQ ID NO:1 or a sequence consisting of nucleotides at positions 4,415 to 7,931 in the nucleotide sequence represented by SEQ ID NO:1, or a sequence consisting of nucleotides at positions 3,820 to 6,068 in the nucleotide sequence represented by SEQ ID NO:2, and has a Period2 gene promoter activity.

As is shown later in Example 1, the sequence consisting of nucleotides at positions 4,415 to 7,931 in the nucleotide sequence represented by SEQ ID NO:1 is an upstream region of the mouse Period2 gene and, as is shown later in Example 3, has a Period2 gene promoter activity.

As is shown later in Example 1, the DNA consisting of a sequence consisting of nucleotides at positions 3,820 to 6,068 in the nucleotide sequence represented by SEQ ID NO:2 is an upstream region of the human Period2 gene. From the experimental results on mouse genes (Examples 1 and 3 which are described later), it was found that the mouse DNA showing promoter activity (namely the DNA consisting of a sequence consisting of nucleotides at positions 4,415 to 7,931 in the nucleotide sequence represented by SEQ ID NO:1) is a DNA resulting from the elimination of the region containing conserved segments (IV, V, VI and VII) in the first intron of Period2 gene from the DNA containing the human/mouse seven conserved segments. Accordingly, it is considered that a human DNA corresponding to the DNA resulting from the elimination of the region containing conserved segments (IV, V, VI and VII) in the first intron of Period2 gene from the DNA containing the human/mouse seven preserved regions, namely the DNA consisting of a sequence consisting of nucleotides at positions 3,820 to 6,068 in the nucleotide sequence represented by SEQ ID NO:2, also has a Period2 gene promoter activity.

Although not particularly limited, the DNA of the present invention can be prepared, for example, by (1) using polymerase chain reaction (PCR) method or by (2) screening a phage library.

(1) Polymerase Chain Reaction (PCR) Method

When the DNA of the present invention is prepared using the PCR method, a primer set capably of amplifying the DNA of the present invention is firstly designed based on the information on each nucleotide sequence represented by SEQ ID NO:1 or 2.

In the case of a DNA of the present invention containing a sequence consisting of nucleotides at positions 4,415 to 7,931 in the nucleotide sequence represented by SEQ ID NO:1, which is the mouse Period2 gene promoter, a primer set is designed based on the information on the nucleotide sequence represented by SEQ ID NO:1 in such a manner that the amplified product contains the sequence consisting of nucleotides at positions 4,415 to 7,931 in the nucleotide sequence represented by SEQ ID NO:1 but does not contain in and after the conserved segment IV (position 8,534). Also, in the case of a DNA of the present invention containing a sequence consisting of nucleotides at position 3,820 to 6,068 in the nucleotide sequence represented by SEQ ID NO:2, which is the human Period2 gene promoter, a primer set is designed based on the information on the nucleotide sequence represented by SEQ ID NO:2 in such a manner that the amplified product contains a sequence consisting of nucleotides at positions 3,820 to 6,068 in the nucleotide sequence represented by SEQ ID NO:2 but does not contain in and after the conserved segment IV (position 6,531).

The DNA of the present invention can be obtained by carrying out PCR using the thus designed respective primer set and a genomic DNA as the template.

(2) Phage Library Screening Method

When the DNA of the present invention is prepared by screening a phage library (e.g., Maniatis, T. et al., *Molecular Cloning—A Laboratory Manual*, Cold Spring Harbor Laboratory, NY, 1982), a probe which can screen phage clones containing the DNA of the present invention is firstly designed base on the information on each nucleotide sequence of SEQ ID NO:1 or 2.

In the case of a DNA of the present invention containing a sequence consisting of nucleotides at positions 4,415 to 7,931 in the nucleotide sequence represented by SEQ ID NO:1, which is the mouse Period2 gene promoter, a probe is designed based on the information on the sequence consisting of nucleotides at positions 4,415 to 7,931 in the nucleotide sequence represented by SEQ ID NO:1. Also, in the case of a DNA of the present invention containing a sequence consisting of nucleotides at positions 3,820 to 6,068 in the nucleotide sequence represented by SEQ ID NO:2, which is the human Period2 gene promoter, a probe is designed based on the information on the sequence consisting of nucleotides at positions 3,820 to 6,068 in the nucleotide sequence represented by SEQ ID NO:2.

A phage clone containing the DNA of the present invention can be obtained by screening a phage library using the thus designed respective probe. The DNA of the present invention can be obtained by treating the thus obtained phage clone with appropriate restriction enzymes and then purifying a DNA fragment of interest using an appropriate purification means (e.g., agarose gel electrophoresis).

[Construct and Cell of the Present Invention]

The construct of the present invention contains the DNA of the present invention and a reporter gene. As the reporter gene, a gene encoding a known reporter protein which can be used as an index of gene expression in the cells can be used. The reporter protein includes luciferase, secretion type alkaline phosphatase (SEAP), green fluorescent protein (GFP), chloramphenicol acetyltransferase (CAT), β-glucuronidase (GUS), β-D-galactosidase, aequorin and the like. According to the construct of the present invention, it is preferable to use a luciferase gene as the reporter gene.

According to the construct of the present invention, arranging positions of the DNA of the present invention and a reporter gene are not limited, so long as the reporter gene is arranged in a downstream position of the DNA of the present invention and under control of the promoter activity of the DNA of the present invention. Also, the construct of the present invention is not particularly limited, so long as the construct contains at least the DNA of the present invention and a reporter gene, but it is preferable that it further contains a vector region.

Although the construct of the present invention is not particularly limited, a construct of the present invention further containing a vector region in addition to the DNA of the present invention and a reporter gene can be prepared, for example, by introducing the DNA of the present invention into a multi-cloning site of an appropriate reporter vector (namely, a vector containing a reporter gene). The reporter vector includes a vector pGL3-basic containing a gene encoding luciferase (Promega), a vector pSEAP2-basic containing a gene encoding SEAP (Clontech), and a vector pd1EGFP containing a gene encoding labile type GFP (Clontech).

More specifically, the construct of the present invention can be prepared by introducing the DNA of the present invention obtained by using the PCR method into a multi-cloning site of a reporter vector.

Also, the construct of the present invention can be prepared by introducing the DNA of the present invention, which has been prepared by treating a phage clone obtained by screening a phage library with appropriate restriction enzymes and then purifying it using an appropriate purification means (e.g., agarose gel electrophoresis), if necessary further subjecting to a blunt-ended treatment, into a multi-cloning site of a reporter vector. For example, in the case of a phage clone containing a sequence consisting of nucleotides at positions 3,820 to 6,068 in the nucleotide sequence represented by SEQ ID NO:2, which is the human Period2 gene promoter, the construct of the present invention containing the human Period2 gene promoter can be prepared by treating the phage clone with appropriate restriction enzymes (e.g., a combination of a restriction enzyme Aor51HI which cuts at position 3,513 position and a restriction enzyme PshBI which cuts at position 6,447), obtaining a 2,935 bp DNA fragment by purifying it using an appropriate purification means (e.g., an agarose gel electrophoresis), smooth-ending the DNA fragment and then introducing it into a multi-cloning site of a reporter vector. A deletion construct containing the DNA of the present invention can be prepared, for example, by treating a longer DNA among the DNAs of the present invention obtained by the above method with appropriate restriction enzymes and purifying the digest by an appropriate purification method and then subjecting the thus obtained DNA fragment of interest to self-ligation. More specifically, it can be obtained by the method described in Example 10.

The cell of the present invention contains the construct of the present invention. Although not particularly limited, the cell of the present invention can be prepared by transforming an appropriate host cell (preferably a eucaryote) with the construct of the present invention (preferably, a construct of the present invention further containing a vector region in addition to the DNA of the present invention and a reporter gene).

The host cell of eucaryote includes cells such as vertebrate, insect and yeast, and examples of the vertebrate cells include mouse NIH3T3 cell, monkey COS cell (Reference 37), Chinese hamster ovary cell (CHO) dihydrofolate reductase deficient strain (Reference 38), mouse L cell, mouse A9 cell, monkey BS-C-1 cell and the like, but it is preferable to use mouse NIH3T3 cell.

The construct of the present invention can be incorporated into a host cell by, for example, a DEAE-dextran method (Reference 39), a calcium phosphate-DNA coprecipitation method (Reference 40), a method using commercially available transfection reagents [e.g., Lipofectamine 2000 (GIBCO-BRL), FuGENE™6 Transfection Reagent (Roche Diagnostics)], electroporation (Reference 41) or the like.

The cell of the present invention can be cultured in accordance with a conventional method. As the medium which can be used in the culturing, various generally used media can be appropriately selected in response to the host cell employed. For example, in the case of the NIH3T3 cell, a medium prepared by supplementing DMEM (Dulbecco's modified Eagle's medium) with glucose (final concentration=4.5 g/l) and fetal bovine serum (final concentration=10%) can be used.

[Transgenic Animal of the Present Invention]

The transgenic animal of the present invention is not particularly limited, so long as the animal is transfected with the construct of the present invention, but it can be prepared based on a conventionally known method (e.g., Reference 35), except that the construct of the present invention is used as the DNA to be transfected. Specifically, it can be prepared based on the procedure described later in Example 4.

Also, the term "animal" as used herein means an animal excluding human (namely non-human animal), and examples include mammals excluding human (e.g., rat, mouse, dog, cat, monkey, pig, cattle, sheep, rabbit, goat, dolphin or horse), birds (e.g., domestic fowl or quail), amphibia (e.g., frog), reptiles, insects and the like, and rat and mouse are preferred, and rat is particularly preferred.

[Screening Method of the Present Invention]

The screening method of the present invention can be carried out using the cell of the present invention, a suprachiasmatic nucleus section or peripheral tissue of the transgenic animal of the present invention or the transgenic animal of the present invention itself. Although the test substance to be used in the screening is not particularly limited, examples include commercially available compounds (including peptides), various known compounds (including peptides) registered in chemical file, compounds obtained by combinatorial chemistry techniques (Reference 31), culture supernatants of microorganisms, natural components derived from plants and marine organisms, animal tissue extracts or compounds (including peptides) prepared by chemically or biologically modifying the compounds (including peptides) selected by the screening method of the present invention.

According to the screening method of the present invention which uses the cell of the present invention, a substance which controls expression of the Period2 gene, namely a substance which modifies its transcription activity, can be selected by allowing the cell of the present invention to contact with a substance to be tested and measuring the reporter activity (namely, a reporter assay).

When the cell of the present invention is allowed to contact with a substance to be tested, a cell into which the construct is temporarily or stably introduced is prepared and drug (namely substance to be tested) stimulation is carried out. A substance which can control expression of the Period2 gene can be screened by carrying out a reporter assay after a predetermined period of time of the drug (namely substance to be tested) stimulation.

The reporter assay can be carried out by a known assay method in response to the kinds of a reporter protein to be used. For example, when a firefly luciferase is used as the reporter protein, luciferin can be used as its chemical substrate for luciferin-luciferase luminescence, and when a *Renilla* luciferase derived from sea pansy is used, coelenteradin can be used as its chemical substrate for luciferin-luciferase luminescence. Also, when SEAP is used, CSPD [disodium 3-(methoxyspiro(1,2-dioxetane-3,2'-(5'-chloro)tricyclo[3.3.1.13.7]decan)-4-yl)phenyl phosphate] and MUP (4-methylunbellifery phosphate) can be used as its chemical substrates for the respective luminescent and fluorescent assay. A luciferase assay is preferred as the reporter assay, and the luciferase assay can be carried out preferably under the conditions described in Example 3 which is described later.

All of the substances which enhance expression of the Period2 gene and the substances which inhibit the same are useful as agents improving rhythm disorders, and when a substance which inhibits expression of the Period2 gene is screened, the screening can be effected by an assay in the coexistence of a known Period2 gene transcription activating factor such as BMAL1/CLOCK heterodimer. A synchronizing factor during daytime has a property to accelerate transcription or release the transcription inhibition (transcription acceleration as a consequence) of the Period2 gene, and it can synchronized the circadian rhythm when reacted in daytime and causes phase shift when reacted in night. Also, a synchronizing factor during night has a property to inhibit transcription or release the transcription acceleration (transcription inhibition as a consequence) of the Period gene, and it has been confirmed that it can synchronized the rhythm when reacted in night and causes phase shift when reacted in daytime. Accordingly, an agent which accelerates transcription of the Period2 gene can synchronize the rhythm when taken during the day, and on the contrary, an agent which inhibits transcription of the Period2 gene can synchronize the rhythm when taken during the night.

According to the screening method of the present invention which uses the cell of the present invention or a suprachiasmatic nucleus section or peripheral tissue of a transgenic animal, a substance which controls expression of the Period2 gene can be selected by allowing the cell of the present invention or a suprachiasmatic nucleus section or peripheral tissue of a transgenic animal to react with a substance to be tested and measuring the oscillatory expression.

There is a report stating that oscillatory curves with circadian cycle can be obtained by continuous measurement of luminescence level from a suprachiasmatic nucleus section or peripheral tissue, under culturing, of a mPer1:luc transgenic rat using a photomultiplier tube detector (Photomal) (Reference 28). When the oscillation of luminescence from a suprachiasmatic nucleus section or peripheral tissue of a transgenic animal harboring a construct containing a DNA showing Period2 gene promoter activity and a reporter gene is continuously measured using this method, and the oscillation of the luminescence becomes stable, a substance to be tested (e.g., a substance to be tested such as a candidate for an improving agent of biological rhythm screened by the screening method of the present invention which uses the cell of the present invention) is allowed to act upon the above suprachiasmatic nucleus section or peripheral tissue of a transgenic animal on one hand, and, as a control, a solvent [e.g., dimethyl sulfoxide (DMSO) or the like] alone of the substance to be tested is allowed to act upon the suprachiasmatic nucleus section or peripheral tissue on the other hand, and the measurement is continued. As the transgenic animal, a transgenic rat is desirable. Phase shift (positional change in oscillation peak or bottom), namely time delay or time advance of oscillatory expression, can be evaluated by comparing the oscillatory curve of luminescence obtained from the group treated with a substance to be tested (e.g., a biological rhythm disorder-improving candidate substance to be tested) with the oscillatory curve of luminescence obtained from the untreated control group. A substance which controls expression and/or oscillatory expression of the Period2 gene can be selected by screening substances showing ideal phase shift in this manner. In addition, the above screening can also be carried out using the cell of the present invention, that is, a cell into which a DNA prepared by ligating an upstream sequence of the mouse Period2 gene with a reporter gene is introduced, instead of a suprachiasmatic nucleus section or peripheral tissue, and synchronizing the cells. The cells can be synchronized by stimulation with high concentration serum or dexamethasone (DEX), but preferably can be synchronized by the method described in Example 6.

For example, a substance which controls expression and/or oscillatory expression of the Period2 gene can be selected by carrying out the continuous measurement of luminescence level from a suprachiasmatic nucleus section or peripheral tissue (e.g., liver, kidney, lung or eyeball) of a transgenic rat (mPer2:luc transgenic rat) prepared by introducing into a rat a DNA in which an upstream sequence of the mouse Period2 gene is ligated with a luciferase gene, by the method described in Example 5 which is described later, and evaluating the phase shift by comparing the oscillation curves of luminescence level obtained from the test substance-treated group with those obtained from the untreated group (control). When it is carried out by the method described in Example 5, it is possible to evaluate the function upon the rhythm of substances to be tested, by changing one suprachiasmatic nucleus section to a fresh medium to which a solvent (e.g., DMSO, etc.) alone is added as a control, and the other to a fresh medium to which a substance to be tested dissolved in a solvent (e.g., DMSO, etc.) is added, at a stage of from the 3rd to 9th day after commencement of the measurement during which the oscillatory expression is observed, and comparing the oscillation after addition of the substance to be tested with that of the control. Also, regarding peripheral tissues, it is possible to carry out screening of substances to be tested by changing medium of, for example liver, lung and eyeball, to a medium containing a substance to be tested (a solvent alone in the case of control) in the same manner, during the 4th and 5th days after commencement of the measurement, during the 1st to 5th days after commencement of the measurement and during the 1st to 3rd days after commencement of the measurement, respectively, during which the oscillatory expression is observed.

Also, as shown in the following Example 5, in peripheral tissues, oscillation rhythm occurred several times and then attenuated by intercellular de-synchronization (cf. FIGS. 7 to 9), and it is possible to obtain an agent showing a function to improve attenuated locomoter activity rhythm and/or sleep rhythm in the aged by screening an agent which inhibits this attenuation.

Also, when a large peripheral tissue (e.g., liver, lung, etc.) is used in the screening, it is desirable to a peripheral tissue section.

According to the screening method of the present invention which uses the transgenic animal of the present invention, a substance which controls expression and/or oscillatory expression of the Period2 gene can be selected by administering a substance to be tested to the transgenic animal of the present invention and measuring oscillatory expression in the suprachiasmatic nucleus of the animal.

Specifically, a substance to be tested (e.g., a substance to be tested such as a biological rhythm improving agent candidate screened by the screening method of the present invention which uses the cell of the present invention) is administered to a transgenic animal harboring a construct containing a DNA showing the Period2 promoter activity and a reporter gene. When luciferase is used as the reporter protein, it is possible to screen a compound by evaluating its function upon oscillation of the rhythm center suprachiasmatic nucleus, by the use of a method in which luciferin is supplied from the vertex into the vicinity of the suprachiasmatic nucleus through a capillary and the luminescence level is simultaneously and continuously measured through a micro-optical fiber inserted into just above the suprachiasmatic nucleus while keeping the individual alive (Reference 42).

EXAMPLES

The present invention is specifically described based on examples, but they do not limit the scope of the present invention. Also, unless otherwise indicated, these were carried out in accordance with known methods (e.g., Maniatis, T. et al., *Molecular Cloning—A Laboratory Manual*, Cold Spring Harbor Laboratory, NY., 1982; and Hille, B., *Ionic Channels of Excitable Membranes,* 2nd Ed., Sinauer Associates Inc., MA, 1992).

Example 1

<Preparation of Mouse and Human Period2 Upstream DNA Sequences and Comparative Analysis>

Preparation of a mouse Period2 upstream sequence was carried out by a screening using a mouse genomic DNA phage library and using Genome Walker Kit (Clontech).

Firstly, polymerase chain reaction (PCR) was carried out by preparing a primer set which can amplify a fragment between a position 218 and a position 723 in mouse Period2 gene cDNA from the reported sequence of mouse Period2 gene (GenBank AFO36893), namely a forward primer consisting of the nucleotide sequence represented by SEQ ID NO:3 [a sequence at positions 218 to 239 in the mouse Period2 gene cDNA (GenBank AFO36893)] and a reverse primer consisting of the nucleotide sequence represented by SEQ ID NO:4 [a sequence complimentary to the sequence at positions 702 to 723 in the mouse Period2 gene cDNA (GenBank AFO36893)]. In this case, the above PCR was carried out using a Taq polymerase (AmpliTaq Gold; Applied Biosystems) as the enzyme and repeating 40 times of a cycle consisting of incubation at 95° C. (10 minutes) and subsequent incubation at 94° C. (15 seconds), 60° C. (30 seconds) and 72° C. (1 minute).

Using the thus obtained amplified fragment (505 bp) as the probe, screening from a mouse genomic DNA phage library was carried out. As a result, a clone containing the first intron of the mouse Period2 gene 6.0 kb upstream from the second exon was obtained. When a sequencing reaction was carried out on the thus obtained phage DNA using a DNA sequencing reagent (BigDye Terminator Cycle Sequencing FS Ready Reaction Kit; Applied Biosystems) in accordance with its manufacture's instructions and then the DNA nucleotide sequence was analyzed using a DNA sequencer (ABI PRISM 377; Applied Biosystems), a sequence consisting of nucleotides at positions 10,104 to 17,004 in the nucleotide sequence represented by SEQ ID NO:1 was obtained.

Next, in order to obtain a further upstream sequence from the phage DNA sequence, preparation of the upstream sequence was carried out using Genome Walker Kit (Clontech). Libraries MDL1 to MDL5 attached to the kit were used as the template of the Genome Walker Kit, and a Taq DNA polymerase (Advantage Genomic polymerase Mix; Clontech) was used as the enzyme for PCR.

Firstly, using AP1 attached to the kit and a first primer consisting of the nucleotide sequence represented by SEQ ID NO:5 (a sequence complimentary to a sequence consisting of nucleotides at positions 13,005 to 13,034 in the nucleotide sequence represented by SEQ ID NO:1) as a primer set, PCR was carried out in the presence of 5% dimethyl sulfoxide (DMSO) by repeating 7 times of a cycle consisting of 94° C. (2 seconds) and 72° C. (3 minutes) and subsequent 36 times of a cycle consisting of 94° C. (2 seconds) and 67° C. (3 minutes) and then finally incubating at 67° C. for 4 minutes. Next, using 1 μl of 50 times diluted solution of the thus obtained reaction product as the template and using AP2 attached to the kit and a second primer consisting of the nucleotide sequence represented by SEQ ID NO:6 (a sequence complimentary to a sequence consisting of nucleotides at positions 12,429 to 12,458 in the nucleotide sequence represented by SEQ ID NO:1) as a primer set, PCR was carried out by repeating 5 times of a cycle consisting of 94° C. (2 seconds) and 72° C. (3 minutes) and subsequent 24 times of a cycle consisting of 94° C. (2 seconds) and 67° C. (3 minutes) and then finally incubating at 67° C. for 4 minutes.

A sequence consisting of nucleotides at positions 9,870 to 12,458 in the nucleotide sequence represented by SEQ ID NO:1 was obtained by sequencing analysis of the amplified band obtained by the above two step PCR. Based on this sequence, a primer set for obtaining a further upstream sequence, namely a first primer consisting of the nucleotide sequence represented by SEQ ID NO:7 (a sequence complimentary to a sequence consisting of nucleotides at positions 10,103 to 10,132 in the nucleotide sequence represented by SEQ ID NO:1) and a second primer consisting of the nucleotide sequence represented by SEQ ID NO:8 (a sequence complimentary to a sequence consisting of nucleotides at positions 10,021 to 10,050 in the nucleotide sequence represented by SEQ ID NO:1), were prepared.

The above two step PCR was repeated except that a first primer consisting of the nucleotide sequence represented by SEQ ID NO:7 and a second primer consisting of the nucleotide sequence represented by SEQ ID NO:8 were used instead of the first primer consisting of the nucleotide sequence represented by SEQ ID NO:5 and the second primer consisting of the nucleotide sequence represented by SEQ ID NO:6, and sequencing analysis of the thus obtained amplified band was carried out to obtain a sequence consisting of nucleotides at positions 9,146 to 10,050 in the nucleotide sequence represented by SEQ ID NO:1.

Subsequently, in order to obtain further upstream sequences one by one, the above procedures, namely preparation of first primer and second primer, two step PCR and sequencing analysis of obtained amplified band, were repeated. Combination of the first primer and second primer used in each two step PCR was, a combination of a first primer consisting of the nucleotide sequence represented by SEQ ID NO:9 (a sequence complimentary to a sequence consisting of nucleotides at positions 9,355 to 9,384 in the nucleotide sequence represented by SEQ ID NO:1), and a second primer consisting of the nucleotide sequence represented by SEQ ID NO:10 (a sequence complimentary to a sequence consisting of nucleotides at positions 9,307 to 9,336 in the nucleotide sequence represented by SEQ ID NO:1);

a combination of a first primer consisting of the nucleotide sequence represented by SEQ ID NO:11 (a sequence complimentary to a sequence consisting of nucleotides at positions 7,838 to 7,857 in the nucleotide sequence represented by SEQ ID NO:1), and a second primer consisting of the nucleotide sequence represented by SEQ ID NO:12 (a sequence complimentary to a sequence consisting of nucleotide sequences at positions 7,818 to 7,837 in the nucleotide sequence represented by SEQ ID NO:1); and a combination of a first primer consisting of the nucleotide sequence represented by SEQ ID NO:13 (a sequence complimentary to a sequence consisting of nucleotides at positions 2,234 to 2,263 in the nucleotide sequence represented by SEQ ID NO:1), and a second primer consisting of the nucleotide sequence represented by SEQ ID NO:14 (a sequence complimentary to a sequence consisting of at positions 2,134 to 2,163 in the nucleotide sequence represented by SEQ ID NO:1), and used in this order.

Also, a further upstream sequence was not able to be obtain by the two step PCR using primers designed based on a sequence consisting of nucleotides at positions 8,918 to 9,336 in the nucleotide sequence represented by SEQ ID NO:1, which was obtained as a result of the sequencing analysis of a DNA band amplified by the two step PCR using a combination of the first primer consisting of the nucleotide sequence represented by SEQ ID NO:9 and the second primer consisting of the nucleotide sequence represented by SEQ ID NO:10. Accordingly, in order to obtain a further upstream sequence, the two step PCR was carried out using a combination of a first primer consisting of the nucleotide sequence represented by SEQ ID NO:11 and a second primer consisting of the nucleotide sequence represented by SEQ ID NO:12, which had been designed based on the first exon sequence.

As a result of the analysis so far carried out, a sequence consisting of nucleotides at positions 1 to 17,004 in the nucleotide sequence represented by SEQ ID NO:1 (however, excluding a sequence consisting of nucleotides at positions 7,858 to 9,145) was obtained. In order to compensate the gap between the first exon and the first intron, which corresponds to the undetermined sequence consisting of nucleotides at positions 7,858 to 9,145, two step PCR (nested PCR) was carried out using a mouse genomic DNA as the template and using a Taq DNA polymerase (Advantage Genomic polymerase Mix; Clontech) as the enzyme. Using a forward primer consisting of the nucleotide sequence represented by SEQ ID NO:15 (a sequence consisting of nucleotides at positions 7,516 to 7,545 in the nucleotide sequence represented by SEQ ID NO:1) and a reverse primer consisting of the nucleotide sequence represented by SEQ ID NO:16 (a sequence complimentary to a sequence consisting of nucleotides at positions 9,063 to the 9,092 in the nucleotide sequence represented by SEQ ID NO:1) as a primer set, the first PCR was carried out in the presence of 5% DMSO by incubating at 95° C. for 1 minute, repeating 35 times of a cycle consisting of 94° C. (15 seconds), 60° C. (30 seconds) and 68° C. (5 minutes) and then finally incubating at 68° C. for 10 minutes. The second PCR was carried out under the same conditions as in the first PCR, except that a forward primer consisting of the nucleotide sequence represented by SEQ ID NO:17 (a sequence consisting of at positions 7,556 to 7,585 in the nucleotide sequence represented by SEQ ID NO:1) and a reverse primer consisting of the nucleotide sequence represented by SEQ ID NO:18 (a sequence complimentary to a sequence consisting of positions 8,977 to 9,006 in the nucleotide sequence represented by SEQ ID NO:1) were used as a primer set.

A 1.4 kbp DNA fragment was obtained as a result of the above two step PCR, and by its sequence analysis, it was able to compensate the gap between the first exon and the first intron.

The nucleotide sequence represented by SEQ ID NO:1 was obtained by summarizing all of the above analyzed results. It was found that the first exon (positions 7,736 to 7,857), the second exon (positions 16,158 to 16,396) and the first intron (positions 7,858 to 16,157) are included in the nucleotide sequence represented by SEQ ID NO:1, and that the translation start site of the mouse Period2 is present in the second exon (position 16,176). Also, the transcription start site is present at position 7,736 (cf. the following Example 2).

Since it is expected that a region important for the regulation of gene expression is conserved between species when upstream sequences of mouse and human genes are compared, an attempt was made to obtain an upstream sequence of the human Period2 gene (GenBank NM-00389). As a result of the retrieval of a draft sequence from a net [BLAST 2; National Center for Biotechnology Information (NCBI)], a clone containing an upstream region of the human Period2 gene (GenBank AC013400.5; 188.2 kbp; phase 1) was found.

Since there was a gap between the first intron and the second exon in this draft sequence clone AC013400.5, PCR was carried out using a human genomic DNA (Clontech) as the template. Using a forward primer consisting of the nucleotide sequence represented by SEQ ID NO:19 (a sequence consisting of nucleotides at positions 14,577 to 14,606 in the nucleotide sequence represented by SEQ ID NO:2) and a reverse primer consisting of the nucleotide sequence represented by SEQ ID NO:20 (a sequence complimentary to a sequence consisting of nucleotides at positions 15,855 to 15,884 in the nucleotide sequence represented by SEQ ID NO:2) as a primer set and using a Taq DNA polymerase (AmpliTaq Gold; Applied Biosystems) as the enzyme, the above PCR was carried out by incubating at 95° C. for 10 minutes and then repeating 40 times of a cycle consisting of 94° C. (15 seconds), 60° C. (30 seconds) and 72° C. (2 minutes), and the DNA sequence of a DNA fragment containing the gap (about 1.2 kbp) was analyzed.

On the other hand, since it was found thereafter that a new clone (GenBank AC012485.13; 168.7 kbp; phase 3 complete sequence) was registered on the net, a region of 17,112 bp (a sequence complimentary to positions 35,354 to 52,465 in the GenBank AC012485.13) corresponding to the 17,004 bp of the above mouse genomic sequence was extracted from the clone GenBank AC012485.13 and shown as SEQ ID NO:2. From the analysis of the thus obtained upstream sequence of the human Period2 gene, it was found that the human translation start site is also present in the second exon similar to the case of mouse. Thus, sequence information on the about 17 kbp upstream from the second exon extending about 17 kbp of the mouse Period2 gene and human Period2 gene was obtained.

The thus obtained sequence information on the upstream regions extending about 17 kbp of the mouse Period2 gene and human Period2 gene was subjected to homology comparison analysis (analyzing conditions are default values) using BLAST 2 SEQUENCES VERSION BLASTN2.2.1 Aug. 1, 2001 program of NCBI. A region having a high Expect accuracy of e-3 or less was defined as positive in preservation ability. Results of the analysis are shown in FIG. 1. As shown in FIG. 1, it was found that seven fragmentarily conserved segments (I to VII) are present in before and after the first exon between human and mouse.

Figure 2:
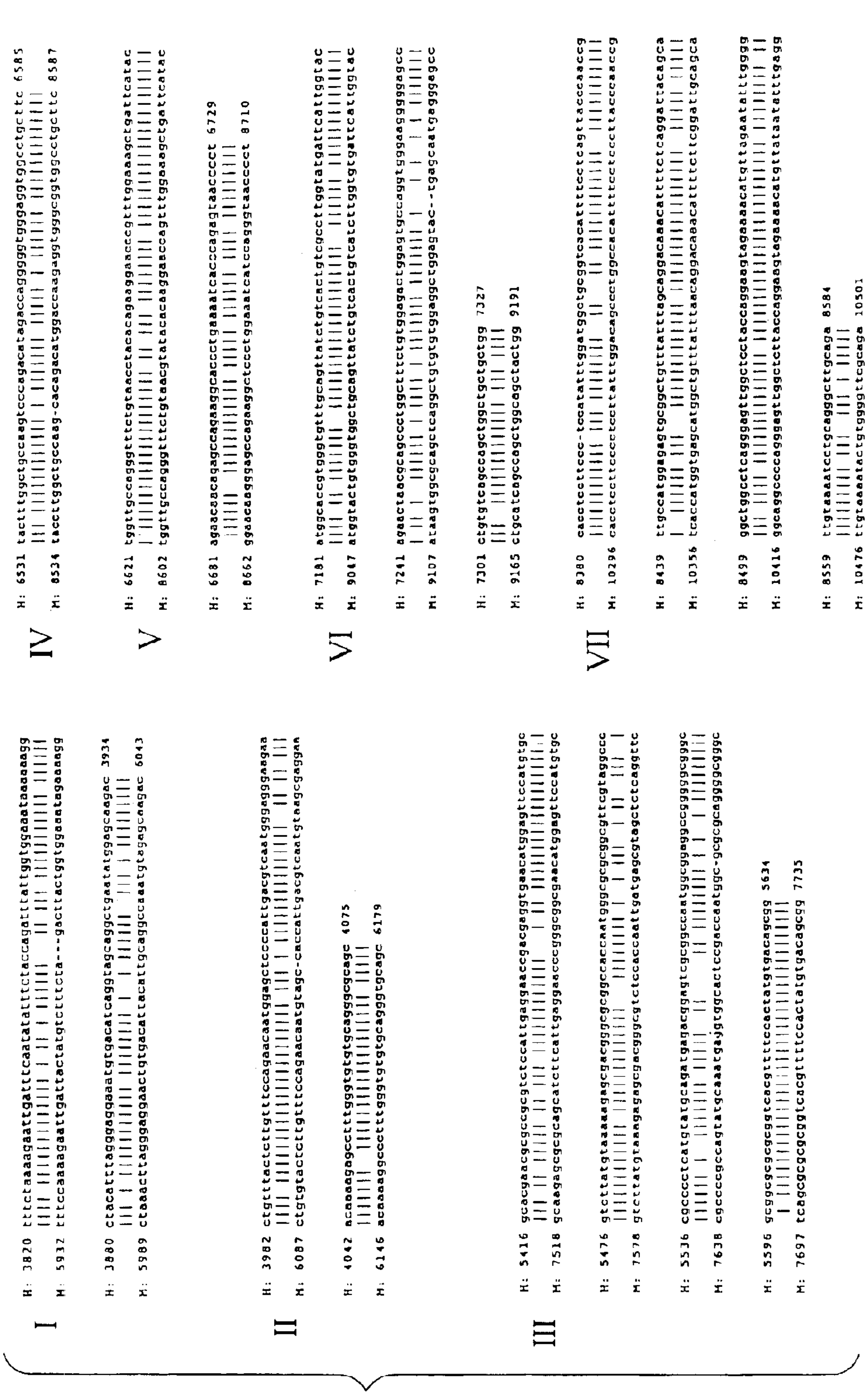
FIG. 2 shows nucleotide sequences of 7 segments highly conserved between mouse (SEQ ID NO. 1) and human (SEQ ID NO. 2).

Respective sequences in the conserved segments are shown in FIG. 2. In FIG. 2, the symbol "H" indicates human sequence, the symbol "M" indicates mouse sequence and the "|" between human sequence and mouse sequence indicates a position where the kind of base coincided between human and mouse.

By summarizing all results of the above analysis, it was found that the first intron (positions 6,069 to 16,461) and the second exon (positions 16,462 to 16,710) are contained in the nucleotide sequence represented by SEQ ID NO:2, and the human Period2 translation start site is present at position 16,481.

When an upstream region DNA fragment is obtained by PCR using a genomic DNA as the template, there is a possibility of causing a gene mutation. An attempt was made to clone a phage containing an upstream region DNA fragment having no mutation from $1\times10^6$ phage particles in accordance the manufacture's instructions of a mouse genomic phage library (Clontech).

In order to prepare a probe, a primer consisting of the nucleotide sequence represented by SEQ ID NO:17 and a primer consisting of the nucleotide sequence represented by SEQ ID NO:18 were designed based on the mouse Period2 gene upstream sequence information obtained in the above. Using a mouse genomic DNA (Clontech) as the template and using a Taq DNA polymerase (Advantage Genomic DNA polymerase Mix; Clontech) as the enzyme, PCR was carried out by incubating at 95° C. for 1 minute and then repeating 35 times of a cycle consisting of 95° C. (15 seconds), 60° C. (30 seconds) and 68° C. (2 minutes), thereby obtaining a DNA fragment of 1.4 kb.

The thus obtained DNA fragment was cloned into the EcoRV site of a plasmid (pBluescript; STRATAGENE) and amplified. This plasmid was subjected to restriction enzyme NotI/SalI treatment and then to an agarose gel electrophoresis to obtain a DNA fragment for probe. Next, the DNA fragment for probe was labeled using [α-$^{32}$P]dCTP (Amersham Pharmacia Biotech) in accordance with the manufacture's instructions of a labeling kit (BcaBEST Labeling Kit; Takara Shuzo). As a result of the screening of the mouse genomic phage library using this probe, a clone containing six conserved segments between human and mouse was obtained. This phage clone in a large amount was prepared, and the phage DNA containing the upstream region was extracted using Phage DNA Extraction Kit (QIAGEN) in accordance with the manufacture's instructions.

In order to obtain a DNA fragment containing seven conserved regions, the thus obtained phage genome was digested with restriction enzymes EcoT221 and NheI and then subjected to an agarose gel electrophoresis to extract and purify a band of a 6.4 kb DNA fragment. The nucleotide sequence of the above DNA fragment is a sequence consisting of nucleotides at positions 4,415 to 10,877 in the nucleotide sequence represented by SEQ ID NO:1. Blunt-ending of the purified DNA fragment was carried out using DNA Blunting Kit (Takara Shuzo).

Since a luciferase vector pGL3-basic (Promega; to be referred to as pGL3-b hereinafter) is a reporter vector having no promoter sequence, it can evaluate the promoter activity of upstream fragments. A vector pCH1 was prepared by digesting this vector pGL3-b with a restriction enzyme SmaI and then inserting the mouse upstream fragment which had been blunt-ended in advance. Subsequently, a vector pCH3 in which the conserved segments (IV, V, VI, VII) in the first intron were removed from the vector pCH1 was prepared by subjecting the vector pCH1 to a treatment with restriction enzymes, XhoI and SnaBI, removing the DNA fragment including the conserved segments (IV, V, VI, VII) by an agarose gel electrophoresis and then carrying out self-ligation. The upstream region sequence of the mouse Period2 gene in the vector pCH3 corresponds to a sequence consisting of nucleotides at positions 4,415 to 7,931 in the nucleotide sequence represented by SEQ ID NO:1.

Example 2

<Identification of Transcription Start Site of Mouse Period2>

Whether or not the vector pCH1 and vector pCH3 obtained in Example 1 containing the mouse Period2 gene upstream region fragment contain a promoter region can be verified by examining the presence of the transcription start site. In order to identify the transcription start site, an attempt was made to identify a cap site using a mouse total brain cDNA library prepared by an oligo-cap method (Reference 32, Reference 33).

Since an adapter consisting of the nucleotide sequence represented by SEQ ID NO:21 is attached to the cap site, a primer consisting of the nucleotide sequence represented by SEQ ID NO:22 (a sequence consisting of nucleotides at positions 1 to 21 in the nucleotide sequence represented by SEQ ID NO:21) and a primer consisting of the nucleotide sequence represented by SEQ ID NO:23 (a sequence consisting of nucleotides at positions 11 to 30 in the nucleotide sequence represented by SEQ ID NO:21) were prepared for the adapter. For the mouse Period2 gene, on the other hand, a primer consisting of the nucleotide sequence represented by SEQ ID NO:24 [a sequence complimentary to a sequence consisting of nucleotides at positions 439 to 459 in the mouse Period2 gene cDNA (GenBank AFO36893)], a primer consisting the nucleotide sequence represented by SEQ ID NO:25 [a sequence complimentary to a sequence consisting of nucleotides at positions 377 to 398 in the mouse Period2 gene cDNA (GenBank AFO36893)] and a primer consisting of the nucleotide sequence represented by SEQ ID NO:26 [a sequence complimentary to a sequence consisting of nucleotides at positions 300 to 319 in the mouse Period2 gene cDNA (GenBank AFO36893)] were prepared.

When a nested PCR containing the first PCR which used the primer consisting of the nucleotide sequence represented by SEQ ID NO:22 and the primer consisting of the nucleotide sequence represented by SEQ ID NO:24 and the second PCR which used the primer consisting of the nucleotide sequence represented by SEQ ID NO:23 and the primer consisting of the nucleotide sequence represented by SEQ ID NO:25 was carried out, a DNA fragment of 414 bp containing the cap site was obtained. Also, when another nested PCR containing the first PCR which used the primer consisting of the nucleotide sequence represented by SEQ ID NO:22 and the primer consisting of the nucleotide sequence represented by SEQ ID NO:24 and the second PCR which used the primer consisting of the nucleotide sequence represented by SEQ ID NO:23 and the primer consisting of the nucleotide sequence represented by SEQ ID NO:26 was carried out, a DNA fragment of 335 bp containing the cap site was obtained.

As a result of the sequence analysis of these DNA fragments, it was found that the transcription start site is present in 8,440 bp upstream (nucleotide at position 7,736 in the nucleotide sequence represented by SEQ ID NO:1) from the translation start site (nucleotide at position 16,176 in the nucleotide sequence represented by SEQ ID NO:1). Based on this, it was confirmed that the transcription start site is contained in the constructed vector pCH1 and vector pCH3, the vector pCH1 has nucleotides of −3,321 to +3,142 (when the transcription start site is defined as "+1") in the mouse Period2 gene, and the vector pCH3 has nucleotides of −3,321 to +196 in the mouse Period2 gene.

Example 3

<Analysis of Promoter Activity and Enhancer Activity of the Upstream Region of Mouse Period2 Gene>

A mouse cultured cell line NIH3T3 was inoculated at $1\times10^5$ cells per well into a 6 well plate on the day before a luciferase assay. Using Lipofectamine 2000 (GIBCO-BRL) as the transfection reagent and using 1 μg of each of various reporter vectors and 20 ng of an internal control vector (PRL-SV40; Promega), transfection was carried out in accordance with the manufacture's instructions. As the reporter vectors, the vector pCH1 and vector pCH3 obtained in the above Example 1, a vector pGL3-b having no promoter activity (Promega) as a negative control and a vector pGL3-promoter in which the SV40 promoter is connected to the upstream of luciferase gene (Promega; to be referred to as pGL3-p hereinafter) as a positive control were used.

Also, the luciferase gene contained in vectors other than the internal control vector (PRL-SV40) (namely vector pGL3-b, vector pCH1, vector pCH3 and vector pGL3-p) is a firefly origin, while the luciferase gene contained in the internal control vector (PRL-SV40) is a sea pansy origin.

After a lapse of 48 hours from the transfection, the cells were washed once with phosphate buffered saline (PBS) and then the assay was carried out using an assay kit (Picka Gene Dual Reporter Assay Kit; Nippon Gene) in accordance with the manufacture's instructions. The luminescence measurement was carried out using Microtiter Luminometer (Dynatech Laboratories).

Figure 3:
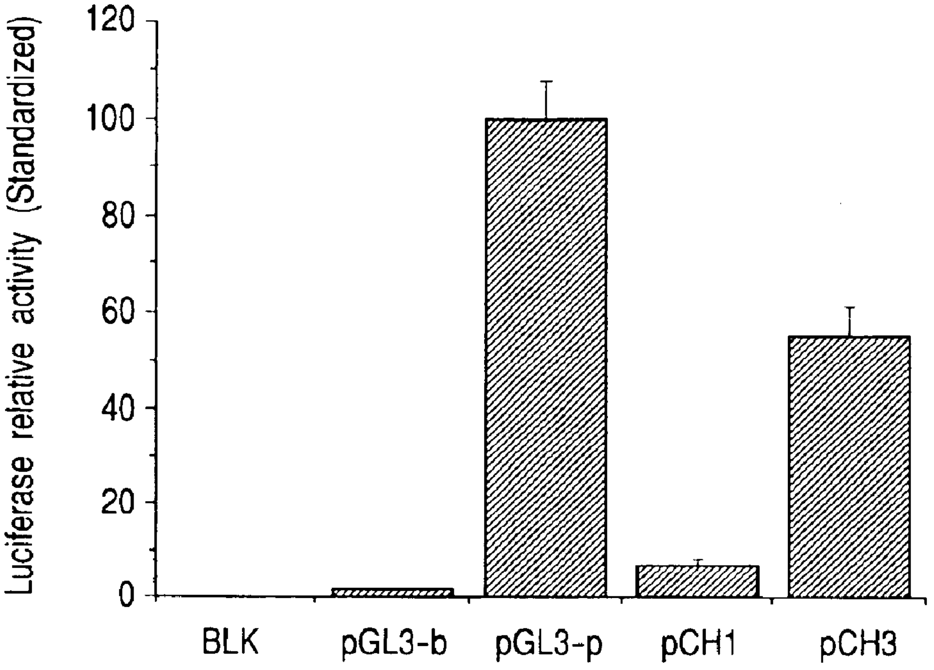
FIG. 3 shows basal promoter activities of mouse Period2 gene upstream regions.

The results are shown in FIG. 3. In FIG. 3, "BLK" means an amount of luminescence in the host cell not treated with transfection. Also, the "luciferase relative activity (normalized)" shown in FIG. 3 means a value normalized based on the expression level of luciferase originated from the internal control vector (PRL-SV40). As shown in FIG. 3, basal promoter activity of the vector pCH1 was a low activity (7% of the vector pGL3-p), while the vector pCH3 showed a promoter activity of 55% of the vector pGL3-p.

In order to evaluate whether or not the vector pCH3 which contains the first exon upstream three conserved segmentss (I, II and III) among the conserved seven sevens (from I to VII) is functional, whether or not the reporter activity of pCH3 is enhanced by a BMAL1/CLOCK heterodimer, which act as a trans-acting factor for Period, was examined.

That is, transfection was carried out using Lipofectamine 2000 (GIBCO-BRL) by adding 25 ng, 50 ng or 250 ng of each of pCl-neo-Bmal1 and pC1-neo-Clock, together with the vector pCH3 (10 ng). Also, the vector pCl-neo-Bmal1 and vector pCl-neo-Clock have been prepared by introducing mouse Bmal1 or mouse Clock, respectively, into a pCl-neo vector (Promega) (Reference 34), and the mouse Bmal1 and mouse Clock are expressed constitutionally in cultured cells. Also, in carrying out the above transfection, 0.5 ng of pRL-CMV (Promega) was added as an internal control, and the DNA to be transfected was adjusted with the pCl-neo vector (Promega) to a total amount of 1 $\mu$g.

After a lapse of 48 hours from the transfection, luminescence level was measured using an assay kit (Pica Gene Dual Reporter Assay Kit; Nippon Gene) in the same manner as the above procedure.

Figure 4:
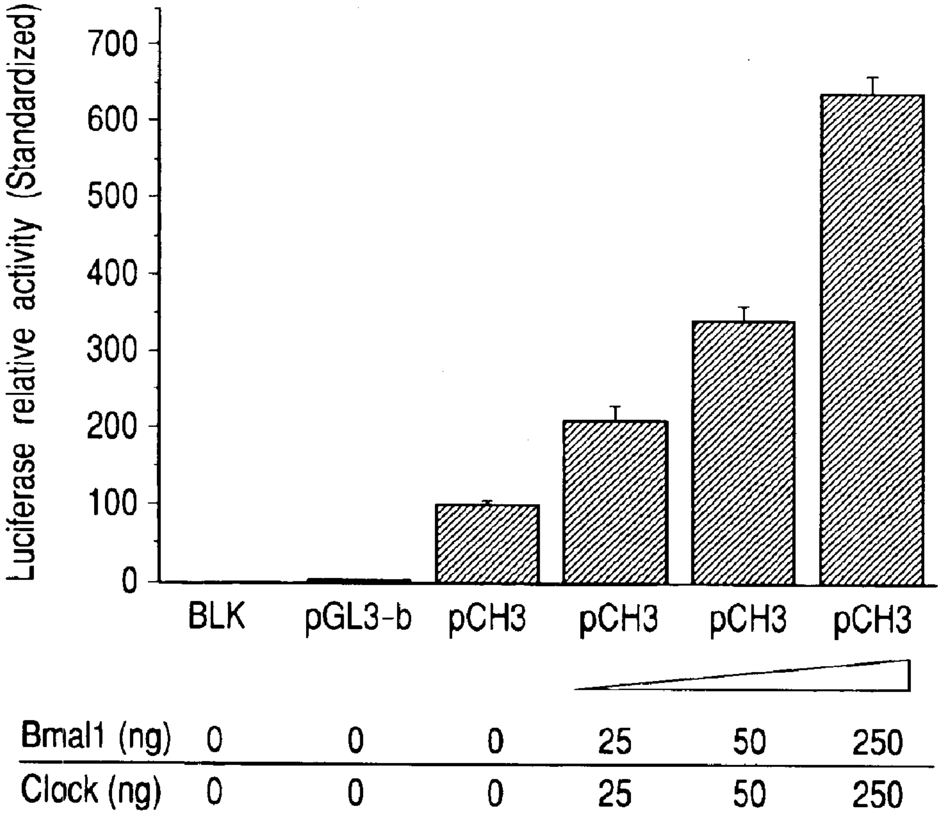
FIG. 4 shows a function of a heterodimer of transcription factors, BMAL1/CLOCK, upon a vector pCH3 containing mouse Period2 gene upstream region.

The results are shown in FIG. 4. The "BLK" in FIG. 4 has the same meaning as the "BLK" shown in FIG. 3. As shown in FIG. 4, dose-dependent transcriptional activation by the BMAL1/CLOCK heterodimer was confirmed. Based on this result, it was found that the thus constructed luciferase vector containing the upstream region of mouse Period2 gene is functional.

Example 4

Preparation of mPer2:luc Transgenic Rat>

Since it is considered, based on the results of in vitro experiments carried out in the above Example 3, that the vector pCH3 contains sufficient elements for showing an intrinsic activity of the Period2 gene expression, an attempt was made to prepare an mPer2:luc transgenic rat using this.

Firstly, in preparing a gene-introduced rat, sequences originating from the vector itself (e.g., replication origin ori, ampicillin resistance gene, etc.) were removed by treatment with restriction enzymes, SalI and MluI, and subsequent agarose gel electrophoresis. Purification of the fragment of interest was carried out using QIAquick Gel Extraction Kits (QIAquick; QUIAGEN), and after carrying out its phenol/chloroform treatment, a DNA solution (concentration=75 ng/$\mu$l) was prepared by dissolving it in 100 $\mu$l of sterile TE buffer [10 mmol/l Tris-HCl (pH 8.0), 1 mmol/l EDTA (pH 8.0)]. The above DNA fragment contains a sequence consisting of nucleotides at positions 4,415 to 7,931 in the nucleotide sequence represented by SEQ ID NO:1 and a gene encoding luciferase.

In order to prepare a transgenic rat, Wistar rats were purchased from Charles River Japan. The transgenic rat preparation operation was carried out basically based on a known method (Reference 35), and micro-injection of the DNA solution for injecting into rat pronucleus stage fertilized eggs was carried out in the following manner.

That is, sexually matured Wistar rats of 8-weeks-old were reared under conditions of 12 hour light-dark cycle (from 4:00 to 16:00 was used as the light period), 23±2° C. in temperature and 55±5% in humidity, and the hormone treating day was selected by observing sexual cycle of females by vaginal smear. Firstly, 150 IU/kg of a pregnant mare serum gonadotropic hormone [PMS Zen-yaku (pregnant mare serum gonadotropin; PMSG); Nippon Zen-yaku] was intraperitoneally administered to female rats to carry out superovulation treatment, 75 IU/kg of a human chorionic gonadotropic hormone [Puvelogen (human chorionic gonadotropin; hCG); Sankyo Zoki] was administered 48 hours thereafter, and then crossing was carried out by allowing them to lodge with males. After a lapse of 32 hours from the hCG administration, pronucleus stage fertilized eggs were collected by oviduct perfusion. The mKRB solution (Reference 36) was used for the oviduct perfusion and culturing of eggs. After removing cumulus cells by carrying out an enzyme treatment of the collected fertilized eggs at 37° C. for 5 minutes in mKRB solution containing 0.1% hyaluronidase (Hyaluronidase Type I-S; Sigma), the eggs were washed three times with mKRB solution to remove the enzyme and then stored in a $CO_2$ incubator (5% $CO_2$, 37° C., saturation humidity) until the DNA injection operation. The DNA solution prepared in the above was injected into male pronuclei of the thus prepared rat fertilized eggs. The injection operation was carried out for 525 embryos, and among survived 431 embryos, 420 morphologically normal embryos were transplanted into oviducts of pseudopregnancy-induced allomothers.

In order to examine whether or not exogenous DNA (including luciferase gene) was introduced into the rats, a primer consisting of the nucleotide sequence represented by SEQ ID NO:27 [a sequence consisting of nucleotides at positions 410 to 432 in the cloning vector pGL3-b (GenBank U47295)] and a primer consisting of the nucleotide sequence represented by SEQ ID NO:28 [a sequence complimentary to a sequence consisting of nucleotides at positions 980 to 1,000 in the cloning vector pGL3-b (GenBank U47295)] were designed as PCR primers for the luciferase gene. Introduction of exogenous DNA (including luciferase gene) can be verified by the presence or absence of a DNA product (591 bp) amplified by the PCR using these primers.

A total of 65 rats were born by the transplantation of 420 embryos. At the time of 3-weeks-old, about 1 cm of the tail tip of each born individual was cut out using a surgical knife and dissolved by adding 800 $\mu$l of a lysis solution and shaking overnight in a 55° C. constant temperature bath. In this case, the above lysis buffer was prepared by dissolving actinase E and protease K, both to a final concentration of 10 mg/ml, in a lysis buffer [a solution containing, as final concentrations, 50 mmol/l Tris-HCl (pH 8.0), 100 mmol/l EDTA (pH 8.0), 100 mmol/l NaCl and 1% SDS].

Subsequently, phenol treatment was carried out twice, and the upper water layer after centrifugation was collected and transferred into a tube containing isopropanol. After mixing, the thus formed filamentous genomic DNA was wound with the tip of a processed glass micro-pipette, soaked in 70% ethanol for 5 minutes and then in 100% ethanol for 5 minutes and finally dissolved by soaking in TE, thereby preparing genomic DNA of each individual.

The PCR which used the genomic DNA of each individual as the template was carried out using a Taq DNA polymerase (Roche Diagnostics) by incubating at 94° C. for 1 minute and then repeating 40 times of a cycle consisting of 94° C. (30 seconds), 57° C. (30 seconds) and 72° C. (60 seconds). As a result, it was found that 8 of the 65 born rats were mPer2:Luc transgenic rats.

In addition, at the time of 7-weeks-old, about 5 mm of the tail tip of each of the 8 mPer2:Luc transgenic rats was cut out using a surgical knife. A luciferin solution was applied to the cut surface, and, turning up the cut surface, the luminescence was measured using a photomultiplier tube detector [Photomal (model name LM-300Y2); Hamamatsu Photonics]. In this case, the above luciferin solution was prepared by adding HEPES (pH 7.2; final concentration=10 mmol/l), penicillin antibiotic (final concentration=25 U/ml), streptomycin antibiotic (final concentration=25 μg/ml), sodium bicarbonate ($NaHCO_3$; final concentration=0.3 g/l) and luciferin [Cat. E1601 (Promega); final concentration= 0.1 mmol/l] to a Phenol Red-free DMEM medium (cat. 13000-054; GIBCO-BRL).

As a result, tails of 4 of the 8 rats showed 923 cps, 4,392 cps, 1,122 cps and 865 cps, respectively. Since these luminescence levels were significantly high compared to the around 100 cps of the control (tail of wild type rat), it was confirmed that 4 animals of the mPer2:Luc transgenic rat in which the luciferase functions in the living body were obtained.

Among these 4 female transgenic rats (FO), the line showing the highest level of luminescence from tail (4,392 cps) was crossed with a wild type male, and 11 F1 rats (5 males and 6 females) were obtained.

Example 5

<Operation of Continuous Measurement of Luminescence Levels from Suprachiasmatic Nucleus Section and Peripheral Tissues (Liver Section, Lung Section and Eyeball) of mPer2:luc Transgenic Rat>

Since the F1 rats obtained in Example 4 are cross-breeds of wild type and hetero transgenic rat, wild type and hetero transgenic rats are included in their legitimate F1 children. In order to select transgenic rats to be subjected to the test in this Example from the above F1 rats, tails of the above F1 rats (namely, the F1 rats obtained by the crossing of the line having the most highest tail luminescence with a wild type, prepared in Example 4) were cut off at the time of 6-weeks-old, and whether or not they show luminescence was examined in the same manner as in Example 4. As a result, it was found that F1 transgenic rats showing significant luminescence were 8 animals (4 males and 4 females). Each of suprachiasmatic nucleus section as a rhythm center and peripheral tissues (liver section, lung section and eyeball) was prepared from one female (7-week-old) among these 8 transgenic rats in accordance with the following procedure, and real time oscillation measurement was carried out.

Firstly, preparation of suprachiasmatic nucleus sections was carried out in the following manner. That is, the transgenic rat was anesthetized under diethyl ether and sacrificed by cervical dislocation, both eyes were excised to block input by light and then excision of total brain was carried out. Unnecessary temporal part, frontal lobe and cerebellum among the total brain were excised, and the resulting brain was fixed on an ice-cooled slicer table with an adhesive (Alon Alfa 201; Toa Gosei). The brain fixed on the slicer table was filled with Hanks buffer [1×Hanks Buffer (GIBCO-BRL; cat. 14060-057) and 10 mmol/l HEPES (pH 7.2) (GIBCO-BRL; cat. 15630-080) in final concentrations], and preparation of sections (400 μm in thickness) was carried out using a slicer (Microslicer DTK-1000; Dohan E M) while ice-cooling. A section containing the suprachiasmatic nucleus was selected by observing under a stereoscopic microscope (SMZ645; Nikon). Preparation of the suprachiasmatic nucleus section was carried out by cutting out the suprachiasmatic nucleus alone located under the third cerebral ventricle from this section using a surgical knife under the stereoscopic microscope.

On the other hand, 1.2 ml of a luciferin-containing measuring medium [prepared by adding 10 mmol/l HEPES (pH 7.2) (GIBCO-BRL; cat. 15630-080), 0.1 mmol/l luciferin potassium salt (Promega), antibiotics (25 U/ml penicillin and 25 μg/ml streptomycin; GIBCO-BRL) and 0.3 g/l $NaHCO_3$ (Wako Pure Chemical Industries), to respective final concentrations, to Phenol Red-free DMEM (Dulbecco's modified Eagle's medium; GIBCO-BRL; cat. 13000-054)] was added to a 35 mm dish, and a membrane filter (MiliCell CM; Millipore; cat. PICMORG50) was floated on the medium. The suprachiasmatic nucleus section prepared in the above was put on this membrane filter to which the medium was supplied from the bottom, and a slide glass cover (40 mm×50 mm; Matsunami Glass Industry) was put on the 35 mm dish and the space between them was sealed by applying a silicon grease compound (Toray Dow Coming) to prevent drying of the medium during the culture. Continuous measurement of luminescence level (real time monitoring) was carried out by setting the 35 mm dish containing suprachiasmatic nucleus section prepared in this manner on inside of an photomultiplier tube detector (LM-300Y2; Hamamatsu Photonics) connected to a computer. The continuous measurement of luminescence level was continued for 20 days, and the measuring medium was exchanged only once during the period (on the 10th day after commencement of the measurement).

Regarding the peripheral tissues, each of the liver, lung and eyeball was excised from the transgenic rat. Thereafter, regarding the liver and lung, tissue sections of about 1 mm square were prepared using a surgical knife and the following measurement was carried out. Regarding the eyeball on the other hand, the following measurement was carried out using the excised tissue as such. A medium was prepared by adding a growth enhancing agent B-27 additive (50×) [B-27 Supplement (50×); GIBCO-BRL] to a final concentration of 2% (1×) to the same above luciferin-containing measuring medium used for the culturing of suprachiasmatic nucleus section, each peripheral tissue (liver section, lung section or eyeball) was directly put into the medium and sealed with a cover glass, and then continuous luminescence measurement was carried out using the photomultiplier tube detector in the same manner as the case of the suprachiasmatic nucleus section. The luminescence measurement was continued for 20 days, and the measuring medium was exchanged only once during the period (on the 10th day after commencement of the measurement).

Figure 5:
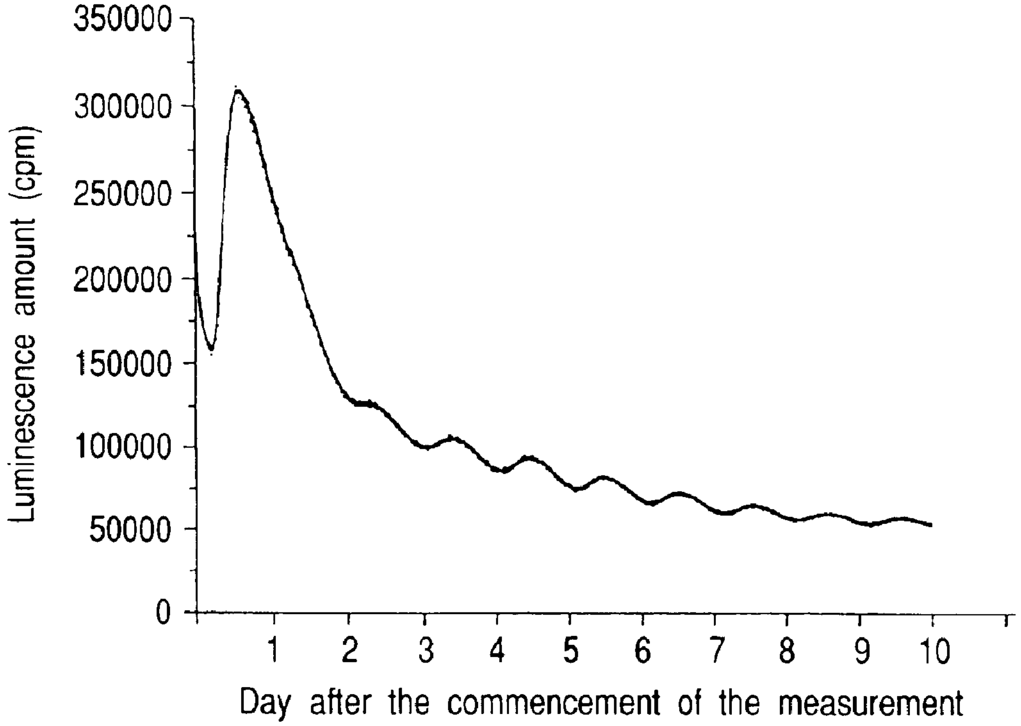
FIG. 5 shows a result of continuous measurement of luminescence from a suprachiasmatic nucleus section, carried out for 10 days after commencement of the measurement.
Figure 6:
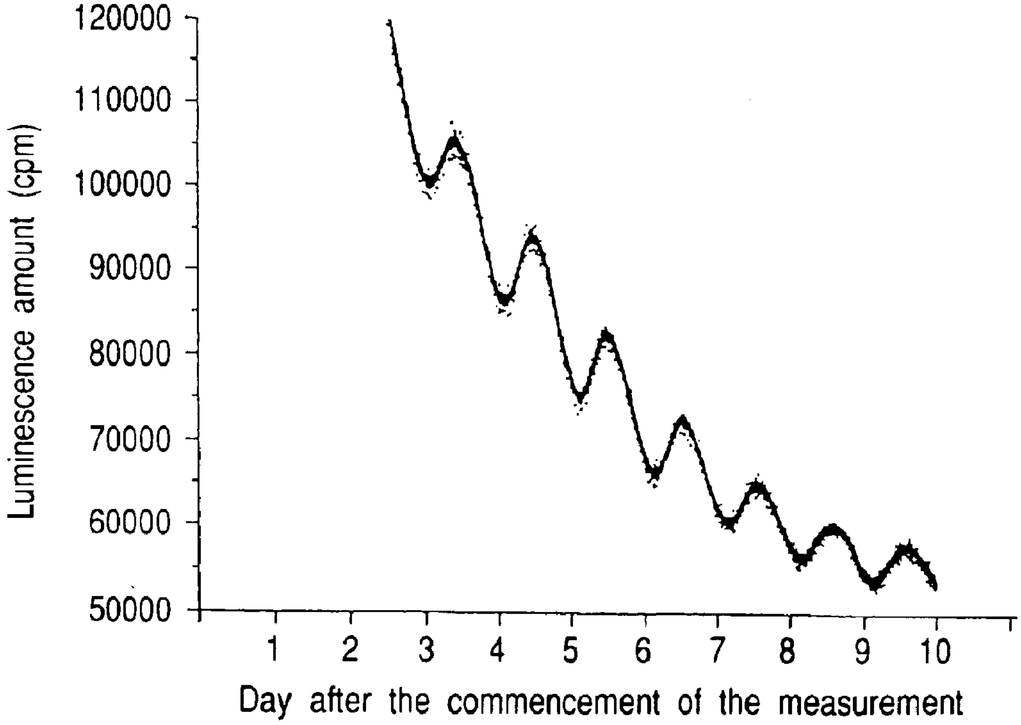
FIG. 6 shows a part of the graph shown in FIG. 5 expanded only in vertical direction.
Figure 7:
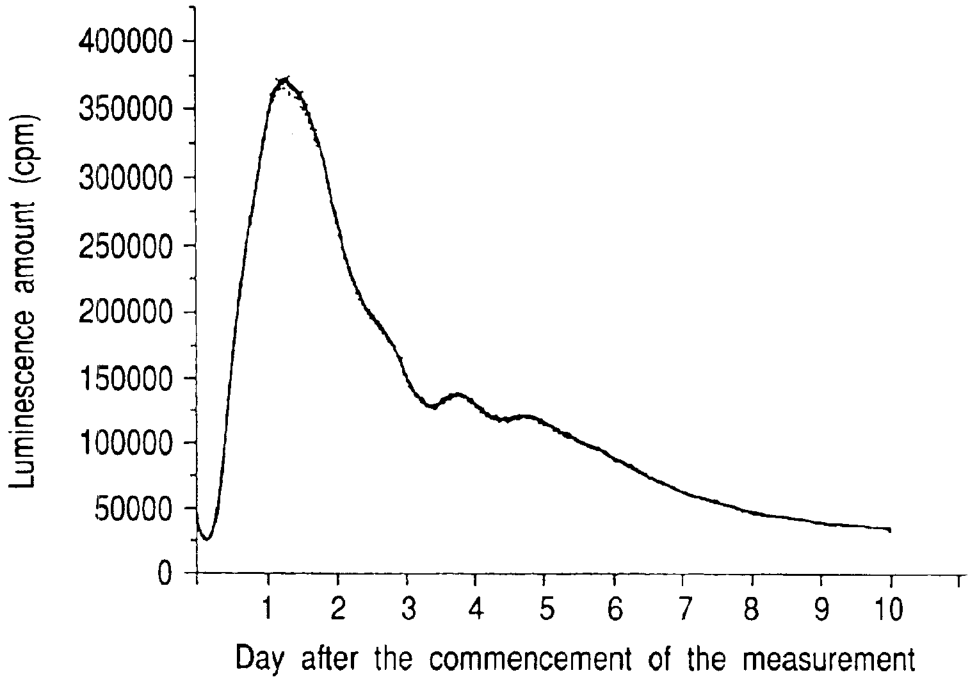
FIG. 7 shows a result of continuous measurement of luminescence from a liver section, carried out for 10 days after commencement of the measurement.
Figure 8:
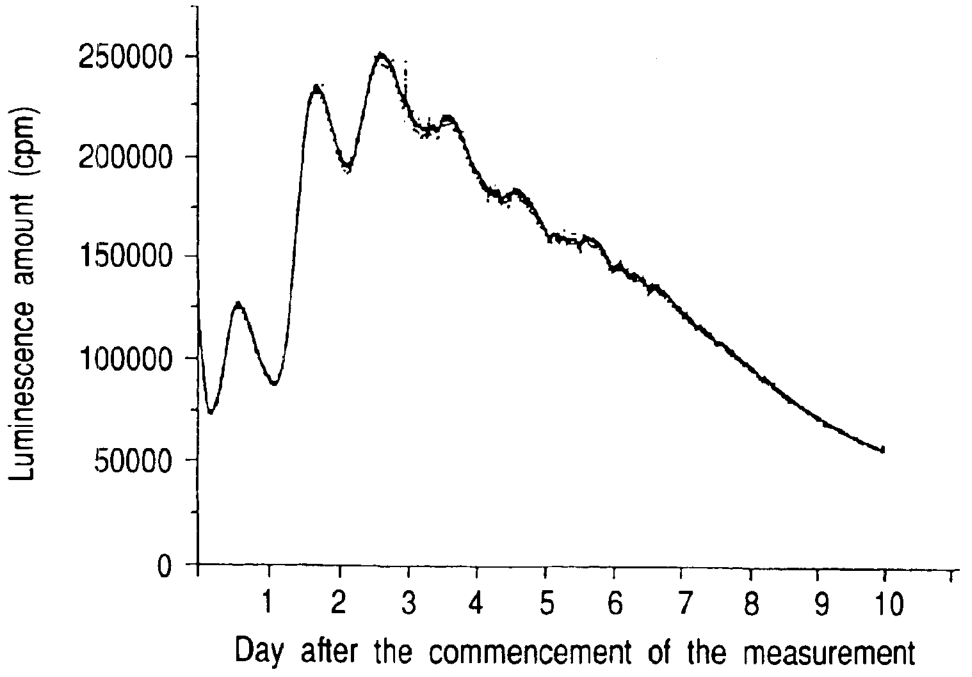
FIG. 8 shows a result of continuous measurement of luminescence from a lung section, carried out for 10 days after commencement of the measurement.
Figure 9:
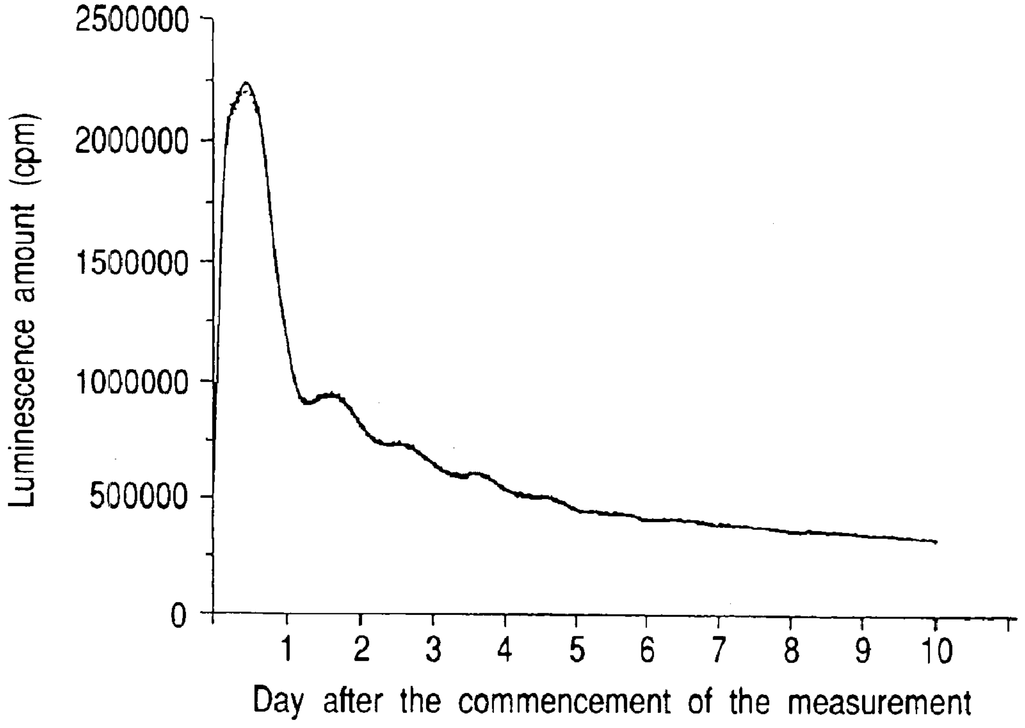
FIG. 9 shows a result of a continuous measurement of luminescence from an eyeball, carried out for 10 days after commencement of the measurement.

Results of the continuous luminescence measurement of the suprachiasmatic nucleus section during the first 10 days (namely from the commencement of the measurement until the lapse of 10 days) are shown in FIG. 5 and FIG. 6, and results of the continuous luminescence measurement of the peripheral tissues (liver section, lung section and eyeball) during the first 10 days are shown in FIG. 7, FIG. 8 and FIG. 9, respectively. In FIG. 5 to FIG. 9, the abscissa shows the number of days from the commencement of the measurement (the measurement starting day was expressed as day 0), and the ordinate shows luminescence (cpm). Also, FIG. 6 shows a part of the graph shown in FIG. 5 expanded only in vertical direction.

As shown in FIG. 5 and FIG. 6, luminescence quantity of the suprachiasmatic nucleus section showed an oscillation peak after about 9 hours on the 3rd day from the commencement of the measurement, and the oscillation rhythm was found thereafter at intervals of about 24 hours. Also, this oscillation continued until on the 20th day after the commencement of the measurement.

As shown in FIG. 7, luminescence quantity of the liver section showed oscillation peaks after about 18 hours on the 3rd day and after about 18 hours on the 4th day from the commencement of the measurement, but the oscillation was not observed thereafter due to its attenuation. In addition, since the oscillation rhythm recovered to 4 times by the medium exchange on the 10th day after commencement of the measurement, it is considered that the attenuation of oscillation rhythm is not due to death of cells but due to de-synchronization among cells.

As shown in FIG. 8, the luminescence quantity of the lung section showed a total of 5 oscillation rhythms after the commencement of the measurement, though accompanied by rapid changes.

As shown in FIG. 9, the luminescence quantity of the eyeball showed an oscillation rhythm having a peak after about 14 hours on the 1st day of the commencement of the measurement, and the oscillation rhythm was observed three times thereafter though the oscillation was small.

Thus, though there are differences in the oscillation phase and continuing frequency of oscillation among respective tissues of the suprachiasmatic nucleus and peripheral tissues (liver, lung and eyeball), the oscillation rhythm after about 24 hours was observed in all of the tissues. It is considered that screening of a substance capable of controlling expression of the Period2 gene becomes possible by the continuous Period2 gene expression monitoring system which uses the transgenic rat of the present invention or its suprachiasmatic nucleus sections or peripheral tissues.

Example 6

<Confirmation of Oscillation-inducing Ability of Mouse Period2 Promoter in Cultured Cell Line>

It has been reported that when a rat cultured cell Rat-1 is stimulated with high concentration horse serum or DEX, a group of cells are synchronized, and clock genes and a group of genes controlled by the clock genes start the 24 hour interval expression oscillation all at once, which continues for several days and then attenuates (Reference 2).

An attempt was made to introduce the above pCH3 construct prepared by connecting a mouse Period2 gene upstream region to a luciferase vector, transiently into the Rat-1 cell, to carry out DEX stimulation thereafter, to change the medium to a medium containing luciferase and then to measure luminescence therefrom real time using the above ultra-weak emission counter. Its illustrative method is described below. Firstly, the Rat-1 cell (purchased from ATCC: designation=Rat1–R12; ATCC number=CRL-2210) was cultured and maintained at 37° C. under an atmosphere of 5% $CO_2$ in a 225 $cm^2$ flask (Iwaki) charged with 2 ml of a medium [prepared by adding antibiotics in respective final concentrations (100 U/ml penicillin and 100 $\mu$g/ml streptomycin; GIBCO-BRL) to Phenol Red-containing DMEM (cat. 11965-092)] containing 10% FBS (fetal bovine serum; JRH Bioscience). The Rat-1 cell was inoculated at $1.2\times10^6$ cells per well into a 35 mm dish (Falcon) on the day before the transfection, and the culturing was continued using 2 ml of the above medium containing 5% FBS. On the next day, 1 $\mu$g of the pCH3 construct was subjected to transfection using a transfection reagent Lipofectamine 2000 (GIBCO-BRL) in accordance with the manufacture's instructions attached thereto. Three hours after the transfection, the medium was exchanged with 2 ml of fresh above medium containing 10% FBS to continue the culturing. Sixteen hours after the transfection, the stimulation was started by changing the medium to the above medium (containing 10% EBS) containing 0.1 $\mu$mol/l at final concentration of DEX (SIGMA; cat. D-8893). After 2 hours of the DEX stimulation, the medium was exchanged with 2 ml of a luciferin-containing measuring medium (the above medium (containing 10% FBS) containing 0.1 mmol/l at final concentration of luciferin potassium salt (Promega)). After addition of the luciferin-containing measuring medium, this was covered with a slide glass, sealed using a silicon grease compound and arranged in the ultra-weak emission counter connected to a computer, and then continuous luminescence measurement (real time monitoring) was carried out.

Figure 10:
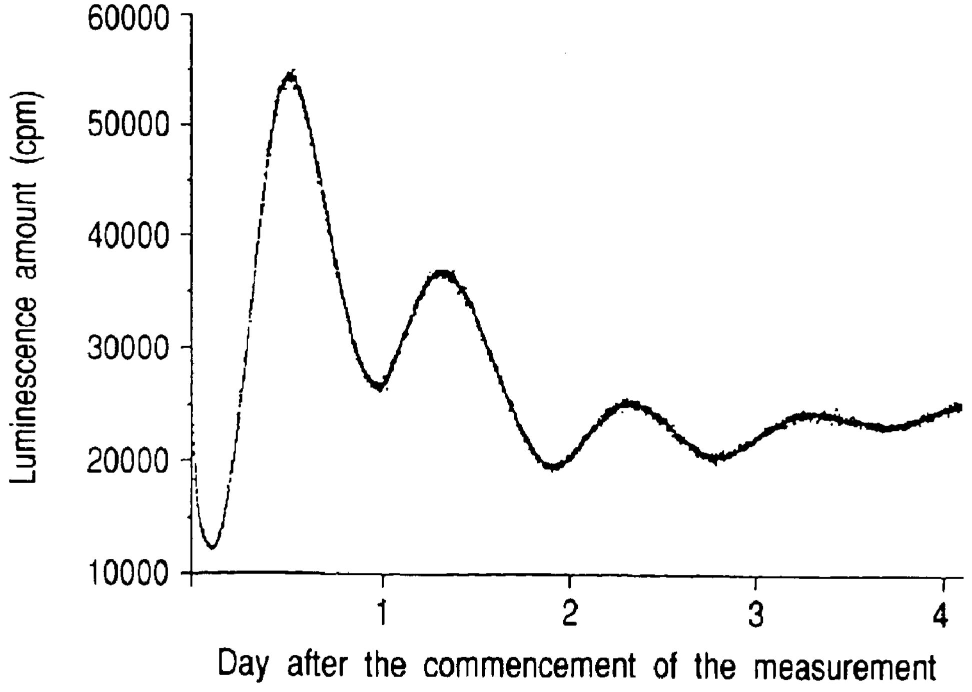
FIG. 10 shows a result of continuous measurement of luminescence from a pCH3-transfected culture cell, carried out for 4 days after commencement of the measurement.

The results are shown in FIG. 10. The abscissa in FIG. 10 shows the number of days from the commencement of the measurement (the measurement starting day was expressed as day 0), and the ordinate shows luminescence quantity (cpm). As shown in FIG. 10, oscillation of the luminescence was observed at intervals of 24 hours. Based on this, it was confirmed that the mouse Period2 gene upstream region claimed by us (positions 4,415 to 7,931 in the nucleotide sequence represented by SEQ ID NO:1) has the oscillating ability also in cultured cells. Accordingly, it is considered that screening of a substance capable of changing the oscillation in cultured cells is possible by the use of this region.

Example 7

<Construction of Construct pTM15 in Which Human Period2 Upstream Sequence is Connected to Luciferase Vector>

From the results of mouse promoter activity analyses of Example 3 and Example 5, it was suggested that the regions I to III among the seven conserved segments are considered to be sufficient for the oscillation. Accordingly, in order to obtain a DNA fragment containing human I to III regions (nucleotides at positions 3,820 to 6,068 in the nucleotide sequence represented by SEQ ID NO:2), PCR was carried out using a human genomic DNA (Clontech) as the template and using a Taq polymerase (Advantage-GC Genomic polymerase Mix; Clontech) as the enzyme. Using a forward primer consisting of the nucleotide sequence represented by SEQ ID NO:29 (a sequence consisting of nucleotides at positions 3,644 to 3,671 in the nucleotide sequence represented by SEQ ID NO:2) and a reverse primer consisting of the nucleotide sequence represented by SEQ ID NO:30 (a sequence complimentary to a sequence consisting of nucleotides at positions 6,402 to 6,429 in the nucleotide sequence represented by SEQ ID NO:2), the PCR was carried out by incubating at 94° C. for 1 minute, repeating 35 times of a cycle consisting of 94° C. (15 seconds), 58° C. (30 seconds) and 68° C. (4 minutes) and then finally incubating at 68° C. for 10 minutes. As a result of the PCR, a DNA fragment of 2.8 kbp was obtained. In general, nucleotide A is added to the 3'-terminal of a PCR fragment amplified by Taq polymerase, so that, in order to carry out efficient cloning of a DNA fragment to which A is added, an attempt was made to prepare a cloning vector in which nucleotide T is added to the SmaI site of the luciferase vector pGL3-basic. That is, the pGL3-basic was digested by treating it with the restriction enzyme SmaI and then subjected to 1% agarose gel electrophoresis, and the digested vector was extracted from the gel, added to a PCR solution containing Taq polymerase (Roche Diagnostic) and incubated at 70° C. for 2 hours for addition of oligonucleotide T to the SmaI cut site. The PGL3-basic TA vector prepared in this manner can clone a PCR fragment efficiently into the SmaI site. A reporter vector pTM15 was prepared by inserting the 2.8 kbp PCR fragment obtained by the above PCR into the PGL3-basic TA vector. The sequence of the upstream region moiety of the human Period2 gene in the vector pTM15 corresponds to nucleotides at positions 3,644 to 6,429 in the nucleotide sequence represented by SEQ ID NO:2 and contains the conserved segments I to III (positions 3,820 to 6,068 in the sequence represented by SEQ ID NO:2).

Example 8

<Identification of Human Period2 Transcription Start Site>

Although it was found in Example 2 that the transcription start site of mouse Period2 is present inside the conserved segments I to III, there is no information regarding the transcription start site of human Period2. Accordingly, in order to identify the transcription start site of human Period2, an attempt was made to identify the cap region using a human cerebellum cDNA library prepared by oligo-cap method (total RNA to be used as the source was obtained from Clontech (cat. 64035-1); Reference 32 and Reference 33). That is, when a nested PCR containing the first PCR which used a primer consisting of the nucleotide sequence represented by SEQ ID NO:22 and a primer consisting of the nucleotide sequence represented by SEQ ID NO:31 [a sequence complimentary to a sequence consisting of nucleotides at positions 480 to 501 in a human Period2 gene cDNA (GenBank NM-003894.1)] and the second PCR which used a primer consisting of the nucleotide sequence represented by SEQ ID NO:23 and a primer consisting of the nucleotide sequence represented by SEQ ID NO:32 [a sequence complimentary to a sequence consisting of nucleotides at positions 122 to 143 in the human Period2 gene cDNA (GenBank NM-003894.1)] was carried out, two DNA fragments of 209 bp and 323 bp containing the cap region were obtained. As a result of the sequence analysis of these two DNA fragments, it was found that the first exon of the Period2 gene exists in two kinds (to be called exon 1A and exon 1B for convenience) which independently connect to the second exon (nucleotides at positions 16,462 to 16,710 in the nucleotide sequence represented by SEQ ID NO:2). The exon 1A is positions 5,625 to 5,773 in the nucleotide sequence represented by SEQ ID NO:2, and the exon 1B is positions 5,806 to 6,068 in the nucleotide sequence represented by SEQ ID NO:2. Thus, it was found that there are two human Period2 gene transcription start sites, and they are present at positions 5,625 (exon 1A) and 5,806 (exon 1B) in the nucleotide sequence represented by SEQ ID NO:2. Based on this, it was confirmed that transcription start sites are contained in the thus constructed vector pTM15.

Example 9

<Confirmation of Oscillation-inducing Ability of Human Period2 Promoter in Cultured Cell Line>

Figure 11:
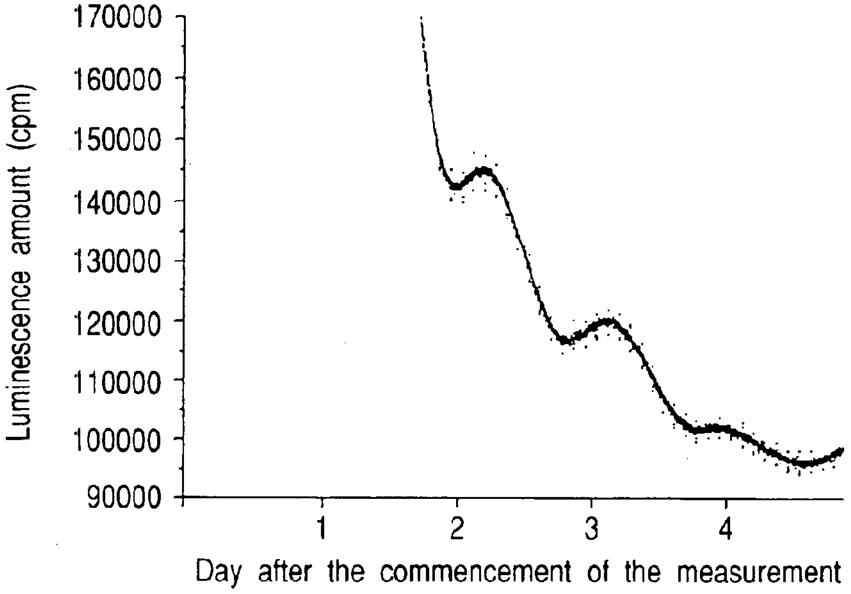
FIG. 11 shows a result of continuous measurement of luminescence from a pTM15-transfected culture cell, carried out for 5 days after commencement of the measurement.

As a result of examination on the oscillation-inducing ability of the human Period2 promoter vector pTM15 in cultured cell by the same method of Example 6, significant oscillation shown in FIG. 11 was confirmed. The abscissa in FIG. 11 shows the number of days from the commencement of the measurement (the measurement starting day was expressed as day 0), and the ordinate shows luminescence quantity (cpm). Since DNA fragment containing the human Period2 gene upstream region claimed by us (positions 3,820 to 6,068 in the nucleotide sequence represented by SEQ ID NO:2) showed the oscillating ability also in cultured cells, it is considered that screening of a substance capable of changing the oscillation in cultured cells is possible by the use of this region.

Example 10

<Preparation of Deletion Construct in Which Mouse Period2 Upstream Sequence is Connected to Luciferase Vector>

It was revealed that the vector pCH3 obtained in Example 1 (contains a sequence of nucleotides at positions 4,415 to 7,931 in the nucleotide sequence represented by SEQ ID NO:1), containing a mouse Period2 gene upstream region fragment having three conserved segments (I, II and III) of upstream of the first exon, has strong promoter activity as shown in FIG. 3 of Example 3 and is transcription-activated by a Period transcription activation factor BMAL1/CLOCK heterodimer as shown in FIG. 4. In order to find that a region important for the basal promoter activity of the mouse Period2 gene and a region important for the transcriptional activation by BMAL1/CLOCK heterodimer are present in which of the three conserved segments, conserved segment deletion constructs were prepared and examined. Firstly, a deletion construct consisting of a shorter nucleotide sequence containing all of the conserved segments I, II and III (correspond to sequences consisting of nucleotides at positions 5,932 to 6,043, 6,087 to 6,179 and 7,518 to 7,735, respectively, in the nucleotide sequence represented by SEQ ID NO:1) was prepared. The above vector pCH3 was subjected to a treatment with restriction enzymes, MulI and BalI, and the digested DNA fragment was removed by an agarose gel electrophoresis. A vector pCH3-D1 was prepared from the vector pCH3 by self-ligation of the thus deletion DNA fragment-deleted product. In the vector pCH3-D1, the sequence of the upstream region moiety of the mouse Period2 gene corresponds to a sequence consisting of nucleotides at positions 5,249 to 7,931 in the nucleotide sequence represented by SEQ ID NO:1 (a nucleotide sequence of −2,487 to +196 when the transcription start site is defined as "+1"). Next, a deletion construct in which the preserved regions I and II were deleted was prepared. The vector pCH3 was subjected to a treatment with restriction enzymes, MulI and EcoRI, and the digested DNA fragment was removed by an agarose gel electrophoresis. A vector pCH3-D2 was prepared from the vector pCH3 by carrying out self-ligation of the thus deletion DNA fragment-deleted product. In the vector pCH3-D2, the sequence of the upstream region moiety of the mouse Period2 gene corresponds to a sequence consisting of nucleotides at positions 6,417 to 7,931 in the nucleotide sequence represented by SEQ ID NO:1 (a nucleotide sequence of −1,319 to +196 when the transcription start site is defined as "+1"). In addition, in order to construct a vector mainly containing the conserved segment III alone, the vector pCH3 was subjected to a treatment with MulI/BstXI restriction enzymes, MulI and BstXI, and the digested DNA fragment was removed by an agarose gel electrophoresis. A vector pCH3-D3 was prepared from the vector pCH3 by carrying out self-ligation of the thus deletion DNA fragment-deleted product. In the vector pCH3-D3, the sequence of the upstream region moiety of the mouse Period2 gene corresponds to a sequence consisting of nucleotides at positions 7,463 to 7,931 in the nucleotide sequence represented by SEQ ID NO:1 (a nucleotide sequence of −273 to +196 when the transcription start site is defined as "+1").

Example 11

<Analysis of Promoter Activity and Enhancer Activity of Deletion Constructs of Mouse Period2 Upstream Region>

A mouse cultured cell line NIH3T3 was inoculated at $1\times10^5$ cells per well into a 6 well plate on the day before a luciferase assay. Using Lipofectamine 2000 (GIBCO-BRL) as the transfection reagent and using 1 $\mu$g of each of various reporter vectors and 20 ng of an internal control vector (PRL-SV40; Promega), transfection was carried out in accordance with the manufacture's instructions. As the reporter vectors described above, the vector pCH3-D1, vector pCH3-D2 and vector pCH3-D3 obtained in the above Example 10, a vector pGL3-b having no promoter activity (Promega) as a negative control and the vector pGL3 as a positive control were used.

Also, the luciferase gene contained in vectors other than the internal control vector (PRL-SV40) (namely vector pCH3-D1, vector pCH3-D2, vector pCH3-D3 and vector pCH3) is a firefly origin, while the luciferase gene contained in the internal control vector (PRL-SV40) is a sea pansy origin.

Forty-eight hours after the transfection, the cells were washed once with phosphate buffered saline (PBS) and then the assay was carried out using an assay kit (Pica Gene Dual Reporter Assay Kit; Nippon Gene) in accordance with the manufacture's instructions. The luminescence was measured using Microtiter Luminometer (Dynatech Laboratories).

Figure 12:
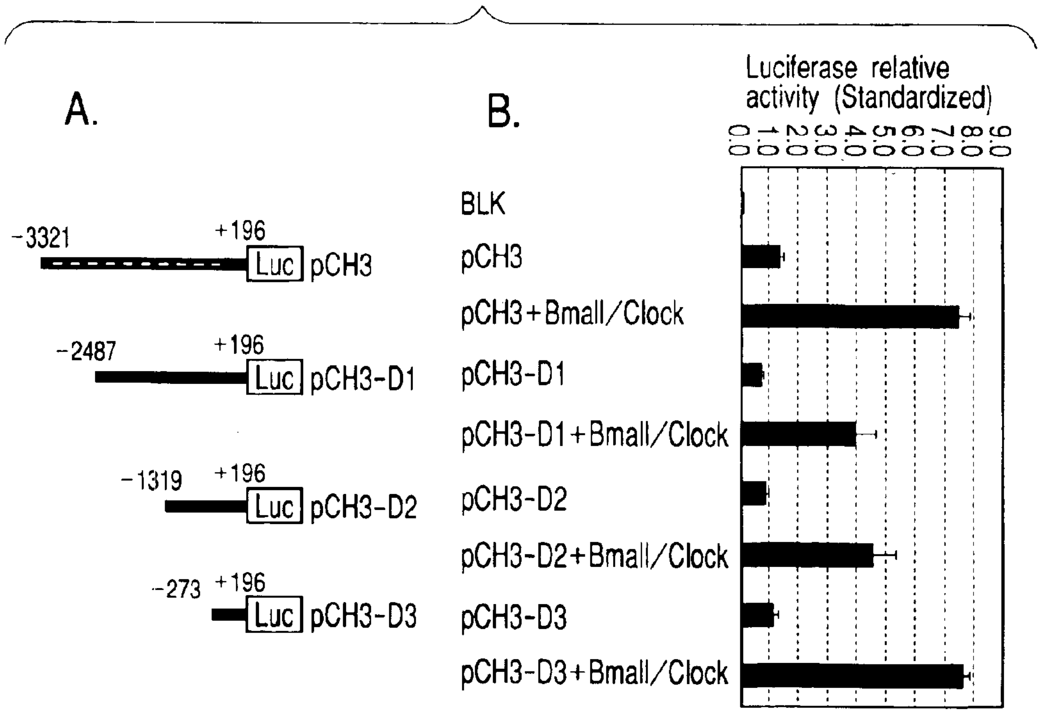
FIG. 12 shows basal activities from various upstream regions of mouse Period2 gene and functions of a heterodimer of transcription factors, BMAL1/CLOCK, upon vectors containing the same regions.

The results are shown in FIG. 12. In FIG. 12, "BLK" means an amount of luminescence in the host cell not treated with transfection. Also, the "luciferase relative activity (standardized)" shown in FIG. 12 means a value standardized based on the luciferase expression quantity originated from the internal control vector (PRL-SV40). As shown in FIG. 12, the basal promoter activity of the vector pCH3-D1 and vector pCH3-D2 showed a promoter activity of about 60% of the vector pCH3. The basal promoter activity of the vector pCH3-D3 showed a promoter activity of about 80% of the vector pCH3. Based on the above, it was suggested that the region carrying out basal promoter activity of the mouse Period is present in a sequence consisting of nucleotides at positions 7,463 to 7,931 in the nucleotide sequence represented by SEQ ID NO:1. When the fact that the transcription start site and the conserved segment III are contained in this region is taken into consideration, it is considered that the conserved segment III is important for the basal promoter activity.

Next, a region necessary for the Period2 to undergo transcriptional activation by the trans-acting factor BMAL1/CLOCK was examined.

Transfection was carried out using Lipofectamine 2000 (GIBCO-BRL) by adding 250 ng of each of pCI-neo-Bmal1 and pCI-neo-Clock together with 10 ng of the above vector pCH3-D1, vector pCH3-D2, vector pCH3-D3 or vector pCH3. In carrying out the transfection, 0.5 ng of pRL-CMV (Promega) was added as an internal control, and the DNA to be transfected was adjusted with the pCl-neo vector (Promega) to a total amount of 1 μg.

Forty-eight hours after the transfection, the measurement of luminescence level was carried out using an assay kit (Pica Gene Dual Reporter Assay Kit; Nippon Gene) in the same manner as in the above procedure.

The results are shown in FIG. 12. The "BLK" in FIG. 12 has the same meaning as the "BLK" shown in FIG. 4. As shown in FIG. 12, transcriptional activity of all of the vector pCH3-D1, vector pCH3-D2, vector pCH3-D3 and vector pCH3 was enhanced 5.0 times, 5.6 times, 7.1 times and 5.6 times, respectively, by the co-transfection of Bmal1 gene and Clock gene, so that it was considered that they received transcriptional activation by the BMAL1/CLOCK heterodimer. Based on this result, it was suggested that the sequence important for the mouse Period2 to undergo transcription activation by the transcription activation factor BMAL1/CLOCK heterodimer is present in a sequence consisting of nucleotides at positions 7,463 to 7,931 in the nucleotide sequence represented by SEQ ID NO:1. Since the conserved segment III is contained in this region, it is considered that a responsive element, on which the BMAL1/CLOCK heterodimer functions, is present in the conserved segment III.

Example 12

<Analysis of Oscillation-inducing Ability of Mouse Period2 Upstream Region Deletion Construct>

Figure 13:
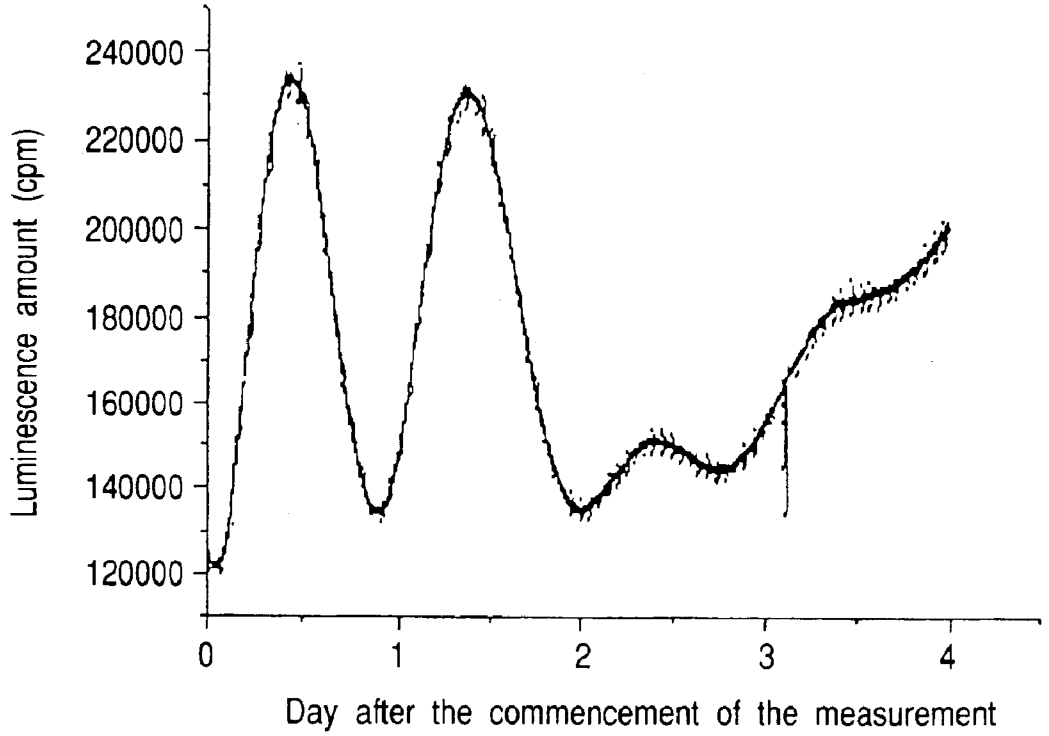
FIG. 13 shows a result of continuous measurement of luminescence from a pCH3-D3-transfected culture cell, carried out for 6 days after commencement of the measurement.

As a result of the measurement of oscillation-inducing ability in cultured cells using the vector pCH3-D3 prepared in Example 10, carried out by a method similar to that in Example 6, significant oscillation shown in FIG. 13 was confirmed. The abscissa in FIG. 13 shows the number of days from the commencement of the measurement (the measurement starting day was expressed as day 0), and the ordinate shows luminescence quantity (cpm). Since a DNA fragment containing only the conserved segment III (corresponds to a sequence consisting of nucleotides at positions 7,463 to 7,931 in the nucleotide sequence represented by SEQ ID NO:1) among the mouse Period2 gene upstream region showed the oscillating ability in cultured cells, it is considered that a sequence important for the oscillatory expression is present in the conserved segment III of mouse Period2 and that screening of a substance capable of changing the oscillatory expression in cultured cells is possible by the use of this region.

INDUSTRIAL APPLICABILITY

A system for the screening of substances capable of controlling expression of biological clock genes can be constructed by using the Period2 gene promoter of the present invention, the construct of the present invention containing this promoter and a reporter gene, the cell of the present invention, the transgenic animal of the present invention or its suprachiasmatic nucleus sections or peripheral tissues. Substances selected by this screening system are useful as candidate substances of agents for improving circadian rhythm disorders (e.g., sleep disturbance, depression or abnormal behavior of patients with senile dementia, caused by abnormal circadian rhythm).

LIST OF REFERENCES

1. J. C. Dunlap, *Cell,* 96, 271–90 (1999).
2. A. Balsalobre et al., *Science,* 289, 2344–7 (2000).
3. S. S. Campbell, P. J. Murphy, *Science,* 279, 396–9 (1998).
4. P. M. Sedgwick, *Postgrad. Med. J.,* 74, 134–8 (1998).
5. N. Kajimura, K. Takahashi, *Nippon Rinsho,* 56, 404–9 (1998).
6. K. Mishima et al., *Acta Psychiatr. Scand.,* 89, 1–7 (1994).
7. A. Satlin, L. Volicer, V. Ross, L. Herz, S. Campbell, *Am. J. Psychiatry,* 149, 1028–32 (1992).
8. A. Tomoda, T. Miike, K. Yonamine, K. Adachi, S. Shiraishi, *Biol. Psychiatry,* 41, 810–3 (1997).
9. C. A. Czeisler et al., *Science,* 233, 667–71 (1986).
10. N. E. Rosenthal et al., *Sleep,* 13, 354–61 (1990).
11. L. Wetterberg, *Intern. Med.,* 235, 5–19 (1994).
12. T. Partonen, M. Partinen, *Acta Psychiatr. Scand. Suppl.,* 377, 41–5 (1994).
13. F. K. Stephan, I. Zucker, *Proc. Natl. Acad. Sci. U.S.A.,* 69, 1583–6 (1972).
14. R. Y. Moore, V. B. Eichler, *Brain Res.,* 42, 201–6 (1972).
15. D. R. Weaver, *J. Biol. Rhythms,* 13, 100–12 (1998).
16. R. J. Konopka, S. Benzer, *Proc. Natl. Acad. Sci. U.S.A.,* 68, 2112–6 (1971).
17. P. Reddy et al., *Cell,* 38, 701–10 (1984).
18. P. E. Hardin, J. C. Hall, M. Rosbash, *Nature,* 343, 536–40 (1990).
19. P. E. Hardin, *Curr. Opin. Neurobiol.,* 8, 642–7 (1998).
20. Z. S. Sun et al., *Cell,* 90, 1003–11 (1997).
21. H. Tei et al., *Nature,* 389, 512–6 (1998).
22. T. Takumi et al., *Genes Cells,* 3, 167–76 (1998).
23. U. Albrecht, Z. S. Sun, G. Eichele, C. C. Lee, *Cell,* 91, 1055–64 (1997).
24. T. Takumi et al., *Embo J.,* 17, 4753–9 (1998).
25. M. J. Zylka, L. P. Shearman, D. R. Weaver, S. M. Reppert, *Neuron,* 20, 1103–10 (1998).
26. D. P. King et al., *Cell,* 89, 641–53 (1997).

27. N. Gekakis et al., *Science,* 280, 1564–9 (1998).
28. S. Yamazaki et al., *Science,* 288, 682–5 (2000).
29. B. Zheng et al., *Nature,* 400, 169–73 (1999).
30. K. L. Toh et al., *Science,* 291, 1040–3 (2001).
31. N. K. Terrett, M. Gardner, D. W. Gordon, R. J. Kobylecki, J. Steele, *Tetrahedron,* 51, 8135–73 (1995).
32. K. Maruyama, S. Sugano, *Gene,* 138, 171–4 (1994).
33. Y. Suzuki, K. Yoshitomo-Nakagawa, K. Maruyama, A. Suyama, S. Sugano, *Gene,* 200, 149–56 (1997).
34. A. Hida et al., *Genomics,* 65, 224–33 (2000).
35. S. Hochi, T. Ninomiya, H. M. A. Yuki, *Animal Biotechnology,* 1, 175–84 (1990).
36. Y. Toyoda, M. C. Chang, *J. Reprod. Fertil.,* 36, 9–22 (1974).
37. Gluzman, Y., *Cell,* 23, 175–182 (1981).
38. Urlaub, G., Chasin, L. A., *Proc Natl. Acad. Sci. USA,* 77, 4216–4220 (1980).
39. Luthman, H., Magnusson, G., *Nucleic Acids Res.,* 11, 1295–1308 (1983).
40. Graham, F. L., van der Ed, A. J., *Virology,* 52, 456–457 (1973).
41. Neuman, E. et al., *ENBO J.,* 1, 841–845 (1982).
42. K. Okamura et al., *Jikan Seibutsugaku Gakkai Kaishi* (Journal of Chronobiology), p. 42 (2000).
43. *Nature,* 409, 684 (2001).
44. *Cell,* 103, 1009–1017 (2000).
45. *Cell,* 96, 57–68 (1999).

Free Text in Sequence Listing

Explanation of "Artificial Sequence" is described in the numerical entry <223> in the following Sequence Listing. Specifically, the nucleotide sequence represented by the sequence of SEQ ID NO:21 in the Sequence Listing is an adapter sequence of oligo cap. The nucleotide sequence represented by the sequence of SEQ ID NO:22 in the Sequence Listing is a sequence consisting of nucleotides at positions 1 to 21 in the nucleotide sequence represented by the sequence of SEQ ID NO:21 in the Sequence Listing. The nucleotide sequence represented by the sequence of SEQ ID NO:23 in the Sequence Listing is a sequence consisting of nucleotides at positions 11 to 30 in the nucleotide sequence represented by the sequence of SEQ ID NO:21 in the Sequence Listing. The nucleotide sequence represented by the sequence of SEQ ID NO:27 in the Sequence Listing is a sequence consisting of nucleotides at positions 410 to 432 in the cloning vector pGL3-b (GenBank U47295). The nucleotide sequence represented by the sequence of SEQ ID NO:28 in the Sequence Listing is a sequence complimentary to a sequence consisting of nucleotides at positions 980 to 1,000 in the cloning vector pGL3-b (GenBank U47295).

Although the invention has been described in the above based on specified embodiments, modifications and improvements obvious to those skilled in the art are included in the scope of the present invention.

SEQUENCE LISTING

```
<160> NUMBER OF SEQ ID NOS: 32

<210> SEQ ID NO 1
<211> LENGTH: 17004
<212> TYPE: DNA
<213> ORGANISM: Mus sp.

<400> SEQUENCE: 1

gccggctggt aaaaagttat ttttcaaatt aaaaccatac ttatactata caaatgtatt     60

atatacaaaa catacataca cacatataaa gttatatttg ttttttacaa ttatttattt    120

gtgtgtgtgt gtttatgtgt gcctacatct gcacttatgt gcccatgtgt accaccaaat    180

ctaggggtca gagactatcc tttgggaatc aacttttctt ccatcatgtg ggtcctgggg    240

tggaactcag gcagttaggt ttgatggtac atgcatttcc ccactgaacc atctcacggg    300

ccctacataa aaatttagaa aatgtaaaga agaaatcatg tttccctata tttcacagag    360

gaaggatgta aaattggggt ttctctttct gctttgcttt ttaagtatat gctacacaga    420

gacaggtgac gtacacacct tgctgttaaa gtgaactcgt tttagaagaa tagcttgcaa    480

acctgggttt ctcagcccaa tatagccttc aaggtaggtg tttcagatgg aggccttcca    540

tggcaagctt tgcttccttg gctcctggga cggagaacag aacaagacat tccaagactc    600

ctgatctttg accccaaggt caaccatctg aggccagaat ggccaggttg gaccaggctt    660

gtgactctga gtggtcagct agtgcatcag aagggtggga agtggataaa ggaaacaccc    720

aatgacttct gtcaacctcc actcccccgc ctcaccccac tccctgccgc caattaccac    780

tgccctgcga cagggtctcc ctcagcctcc gttgccttga gagaacatat tgtgttctcc    840

aagagtagaa gtggtgtcca ctccttgtca ctgcaacaca tccaaagctc tcattctgtt    900

gttgcacctg cgctccagag aaatctgagt ccaaggggca caaggtctcc atgaccttga    960
```

-continued

```
gaggtgactg gtgaggagca cttgattgag agtatttcat gacaagggtc ccactttcag   1020
tcttctttac agaagttggg aagattgctt tctagctaat gaatccaaga aagctggttt   1080
ctcactgcaa ctgaacagag acaactctta tttgctgggg acatgttctg gtagccacgc   1140
agatctgagc cagggctgga gactgagtgc ctctccatct atatggcctt gattgtcacc   1200
actttgctaa tgggtcatgg tggcagctga gacatggtca ctgtgggtct tccttccttc   1260
cttccttcct tccttccttc cttccttcct tccttccttc cttccttcct ctctctctct   1320
ctctctctct ctctctctct ctttcatcat agaaataggt acatgctgta aaactttggc   1380
ttccttttc tgctccccca cccccctctt tagcaaacca ggttgttaaa cattcactac   1440
cactctgttg gagtcactat cagaatcgag tggaattagc tcctggtgcc tctgccagac   1500
actgcagaag gcacactcca catcacagag gagagctgaa aggaatgcaa gttgagccct   1560
gctctccatc ccccaggctc agtgaagatc cattatccta caagtgctgc aggcctccca   1620
gccagctctg cagctctgtg gctactggac tagctcctgc cagagtgggc ttaggctctg   1680
gcaggcttga actgccccta gctggaggcc tgtaacctga gaggtgaggg aaggttagag   1740
gcttaagcca aataccaccc tgcaggcacc tgacccacag gaaggatcag gcaagagcag   1800
aatcctctgg ggaagtaatg gctcctgctg cattgaggag acttgaaggg gtaagattct   1860
tagcccacct acctacaagg tctatatcac agggtcaggg tcacatttga acactgggtg   1920
tctgtcaagg ctgggatttg ggtctctgat cccaggcccc tagttctagg tctgattttt   1980
caataatcta cctagtacta taggagatta aaatttccta agactgcctt agagccctaa   2040
ggttttcaaa atttgtctta aatgggagat taactgtcct aagccctttc ctttcccatt   2100
tgtccaggtc cagaatcaaa cacaagccac cttcttcact gtcattgcca ttgccaccgc   2160
tctcaccaag cattgcccag tgccttgttc cctctttgcc ccaccccatt acagccgtct   2220
agaggtaaaa tgtctagtaa ctgcagtgct accaatgact aggttattag cagggatcac   2280
gaaaaccttt cctgcaaagg gtcagatagt aaacagtctc agctaatagg ctctcttggc   2340
agagtcacaa tagcatcctg ggctttctt ccctctcccc tttcccttta actcgcaggc   2400
tatgccaaag ctggcctcga gccagatttg actgccaagc catagtttaa tgatctctgg   2460
tgattatggt ctcacaggga caggtgagct tggaaatgct ttgtgtctta caatgtgact   2520
cgtccctcaa agttccatgt ctagggagcc tggtcctcag tgtggtgaca ttgggacgtg   2580
ctgtgcacct tttaagaggt ggggacaggg gaaggtcctt agatcattga ggctgctgag   2640
gatcaaggta gagggcatga aacatatttg gttatttctg gagtaagggc cttttatcat   2700
ctccctgtct ttattcctag tgatgtaacc cctccttcgt gggtgtgctc ctgctacagt   2760
gccatccaat acgaggttct caccaaagcc ataatccgag ggccacctga tcttggactt   2820
tcggtcttca aatctgtggg ttacataagc ttcttttctt cacaaagtag cctctctcat   2880
attacatcgc agtgttgaaa acagatcagt cgtgcatggt aagcggttca attccggact   2940
gagatcttgg ctaagaagat acttacagaa gcttgtctag tctccagtgt ttcatcttgg   3000
agttcttttg agggcagctc agtgaggccc atttgttatt ttctacaagc cttggtctgg   3060
gaacagttag tggtgttttt ccatgttagg ctttaacaag tcagcaggag acggcaaccc   3120
ccaaaccaca cggtactcag cgggcttgga aaagacctca ctaaagggta ggcttgtagg   3180
cagagaacca ggcaaggctc gcagtgaccc tgggagcttg tcctgctaga agattcatgg   3240
cagcctgaca cagctagagg ggtgagtcag gggtagtaac ccacaaggaa aaccttttct   3300
ccagccttta taggtttaga aggaaatcag aagaactcgg ggtacacttt gccagccaca   3360
```

-continued

```
tcacaatggg cttcctgctg gagagaatat tccagagaca gtccgttgga gcttggactt   3420
tgcacaacca taacctgtgc cttttccttt cccaggctct gtagggtgga gcggcgaggg   3480
tgatcatgag ctcatgctgc agacaaaggt catcggtggc atgattcctg ccacattgag   3540
atttgggaat gtcttgtgcg aaggagcagt ggggatacgc atacaccttg tacagctgtg   3600
aggattaagt aagagatggc acgttagtgc caagcacgac tcctgtgagt gtggggcaat   3660
cacagctttg tgcagtcaag gcaggtcctt aatggccata gccatccgtg aatatgaacc   3720
ttcggtctca gcctcctgct ttcttctgtg tcacccaggt taaataccct gttagtgact   3780
acctttgatt ttcctcaggg catgaaaggc ctacattcct gatgctactc cacgacatct   3840
atgttagggg gagggaagga gagcagagaa gctgtcattc agtaccacta acaatgctgg   3900
aagaaggaga ctgaggtgac tttcttgggg acacatgagt agaagaggat aggacaagag   3960
ggacttctag gaaaatccta tggcttagag gatagtgaga tcagcccttt actaatagga   4020
aagcctttct ccttgtgagg gaagaagatt ctcatatatg gggatcactt caaacatgag   4080
gataacaaac aatgaaatca cttcagacat ggaggatcac cttaaacttg aaagattatc   4140
ataggtatgg aggattacct tagacatgga ggatcacctc agacatggag gatcacctca   4200
tacatagagg atcacctcag acatggaggg tcacctcaga tatgatcacc ttagacatag   4260
gggaatcacc tcagtcatag aggatcacct cagacatgga ggatcacctc agacatggaa   4320
gattaccata aacataaagg tcacctcaga taatggaaga ttacctcaaa tatggagaat   4380
cacctcagat atagaggatc acctcagaca tgcatgcagg tgtgcctttc accttagctg   4440
tggtgtcact ttggacacaa cgtgtatgta agtttcatca ttgtaacaaa tgcacaaggc   4500
agttggttta taaggagaaa aagtttactt gggcccctag ttctgaaggc ttcagttcat   4560
aactgattat cactgttact ttttggtcta tagcaagggc aagtgatcac tgtaccagca   4620
tgtgggaaat agttgacttc atgactgaaa cgagagggag ctatttcaca gtccctttaa   4680
gggcatttct ccaattacct aaaacctcct cctaggaccc actcctccaa ggcctcacca   4740
cttcccagtg atagcatgtt ggtaacctat tctttaatgt acaggtgttt gaagacattc   4800
cagagccaaa ttatagcagg atttcacctt gagtatgggg gatcacctgg agtgtggaga   4860
ctactccagg tccaaggatc aatcatctca gacgtgggac agtttatagt ttgaacgtga   4920
tatatttccc accagctctg gtgtttgagc acttagccct tcggtgttgg tgtcattttt   4980
ggaggttgta gaacctctga gggaaccaca tacatggtgt acagatatac atgcagtcaa   5040
aatatacata cacacaaaaa ttttaagaaa ataaaagtaa gtgatacagg gcattgcctc   5100
aggcattggg tgttatatca gacatgaggg acactcaaga catggggagc acctcgtagg   5160
tagtgcatca ccttggacac agttgtcttg tgacaaaatg tcttcctgtg ggccccttca   5220
aaactgtgag agatatgagt ggccacaaaa ccctggaaag aatctcaaac cctggaaaga   5280
gtctcagaaa accttgatcc acaactcaat tcccaagttc ccaaagcttg atctacagca   5340
ccaactccca gaactgtcat ccacatgact acccatcccc caccaaaaga cacaactctt   5400
atctcagtca agccattggc tgtccttata accctgaaac ttgatgcttc aatctcttct   5460
tgcatagcat ggcagcaaat agttttagtc tgggaggagg ctttttttaaa aactgtgtct   5520
tcagggctga agagatagtt tagcagttaa aaatacatat tgcctttacg gaggactcag   5580
gttttggttt ccagcaccca tgtggcagct cacaacaatc tataactcaa gccagtgtgg   5640
gatacagtgt aaaaatccaa accgggtgtg gtggcgcacg cctttaatcc cagcactcgg   5700
```

-continued

```
gaggcagagg caggcggatt tctgagttcg aggccagcct ggtctacaaa ctgagttcca   5760

ggacagccag gactatacag agaaaccctg tctcaaaaaa aaaaaaaaaa aaaaaaaaaa   5820

aaaaaaaaaa agaaagaaag aaagaaagaa agaaagaaaa gaaagaagaa tccaaccaaa   5880

accagagaca aattagattc caaagagttc tagagtcccc acagtattgt gtttccaaaa   5940

gaattgatta ctatgtcttt ctagacttac tggtggaaat agaaaaggct aaacttaggg   6000

aggaactgtg acattacatt gcaggccaaa tgtagagcaa gacaagaaaa agctgagcat   6060

gaaggagact ctgccaggtg gatgagctgt gtactcttgt ttccagaaca atgtagccac   6120

cattgacgtc aatgtaagcg aggaaacaaa aggccctttg ggtgtgtgca gggtgcagct   6180

tggcccagct ctgctcagtg tttgtgtgtg ttggggagtg tggtgaggtg tcagtgtcag   6240

aggaaccaga ggtgctgccc tgccccctgc agtgtgagtc aacatctggc ttcccagggc   6300

ttctttggaa agggctgctg aaatgaactt agtctctgcc cccatctgca tctgaggaat   6360

tgcatgcctg tcctgccagg cagacagaaa gaagtagctc ccacacggaa ttcttgaatg   6420

tgggttagcc ggctgtgtac accagcagct cagtttgtta gcagacttct gttgctaatg   6480

tttgcctcct ttccattcct ggttcctagg acaccccagg ggaagattca gagtagtgga   6540

tgctactagg cttcaagttc cctggcaatg acaaatgacc tttttaccct tggaagacgt   6600

gacaagcttg ccttctccat cacaccttgc atgagtcttt aggttgttct ctgtcagcct   6660

caaacccgct ccgaggaaac ttctactccc tcctttgacc ctctggacag gagcctgaac   6720

gctttagtag gcttccagac agtgctcttg aaagaaccaa atagcttcaa ccaaggttcc   6780

acaggggcag ggctgtccta tcactggagg agtaccctcc cctgactagc tagtgtctgt   6840

agcttccact tcagaaaagc cctgctgttc cagatgcaca ccccgcttcc atagttcctg   6900

taaggttaat aaactacacc accgcatttg gttaagcttc cctgtagaac gtcagtcttc   6960

tctccctatg tgattgaggg caggaagaaa tcacttcttt cctttgtatc tctgcacggc   7020

aattatgacc ttatttcctg aatcaacact aactagcaac acgcagtttc agaaacaaga   7080

aaggctaagt gggagttttg tgctttggcc catctggaat gacggtcagc ctgggggcc    7140

tgtcctaggg tcacccagcc tgtcctggga aggtgctcag cagcagatcc agaggggccg   7200

tcctatttgt cctcaagcgt ctcgccatga atgaatgaga ggggaaatga atgaactggg   7260

ctggatgagc gaaaggtgtc agcagagagc attctcggtc cttcagatta ccgaggctgg   7320

tcacgtcgtc gcaggtgata ggccggtggc cctggtctct gccggctgtg agttgcgcag   7380

cggccaagca ccattccccc gcgccgcagt ggtacgcgcc actccggggc tgcacgagcc   7440

ggccaccgcc gtgccaggtg aatggaagtc ccgcaggccg gaagtggacg agcctactcg   7500

cccgggcgcg ggggggcgca agagcgcgca gcatcttcat tgaggaaccc gggcggcgaa   7560

catggagttc catgtgcgtc ttatgtaaag agagcgacgg gcgtctccac caattgatga   7620

gcgtagctct caggttccgc cccgccagta tgcaaatgag gtggcactcc gaccaatggc   7680

gcgcgcaggg gcgggctcag cgcgcgcggt cacgttttcc actatgtgac agcggagggc   7740

gacgcggcgg cagcggcgct actgggacta gcggctccgg gcggctgcgg cgcaggccga   7800

gcgcaccaag tgacgggccg agcaagggac agacgcgcgg gttgacgcgg cgaagcggtg   7860

agtggcgcgg cgctgggcgg tggcgcggtg ctgggcggtg gcgcggacct ggacggccgt   7920

ggtcgtctta cgtaaccggc ggctcggaca gctggagctg gggtcctgag ccaggagttg   7980

ccgactgtgc aaacggctgc aactcggcag aatgtagatg gaactgcgcg gtgacccttt   8040

tccaggttca cactgctgtc cccatttctc aggttaggca ctgaggtcgg agagattagt   8100
```

-continued taggcatctt gtccgaggac acagagacat tgagtgatca cgacaccaga ctgagcacgc 8160
cgactcccat ggtgctgtcc aaggaagcca gggtcagtgc aaactgttcc taggatgggt 8220
ccagagggtc ccctaaggag ctggcttcct gctatgagtt cagagagtca agtctggccc 8280
tgggggaagg accactggta ggcactgact cccagcggtg ggaaaggggt taaacagaga 8340
aatacccagt gccaagccac acctgcccct ccccgcccct atgtcaggga gaccactttg 8400
tccacccact ttgatttccg tggcatcctc cacgccagta tttcctgtct ccagatggac 8460
tgggagtatg tcaggagagg ggggagaggt ccactcttaa gctggagcag tcacatcgtc 8520
atcctttgag acataccttg gctgccaagc acagacatgg accaagaggt gggcggtggc 8580
ctgcttcttc tgcaagaacc ctggttgcca gggtttctgt aacgtataca caaggaacca 8640
gtttggaaag ctgattcata cggaacaagg gagccagaag gctccctgga aatcatccag 8700
ggtaacccct agcttgaaga ggcacagcca caggctggca agctgtacca ctgtaaaaac 8760
caggcctggc agtctcagga tctgtttctc ctccttggtc cacatgctta ccagaggtgc 8820
aaacctgaag ggaagcatgt ccactctgtc ttagtctctg gagtctaggt cggattcgtc 8880
tgataaccag agtctgtctg cctcaaggct ttaatttaaa aaagtcggtt ttgtgtgtgt 8940
gtgtgtttta agatacggaa agcaccactt tgtgtacgtt gttggaatct aagaaagcca 9000
gggactcctt tattttaatg gtagctgtac agtgtgcccg aatggaatgg tactgtgggt 9060
ggctgcagtt atctgtcact gtcatcttgg tgtgattcat tggtacataa gtggcgcagc 9120
tcaggctgtg tgtggaggct ggagtactga gcaatgaggg agccctgcat cagccagctg 9180
gcagctactg ggtacctcgg cttaccctgg gctccagttt cctcatctga gacagtctct 9240
gagatctggc cctgtgcacg tttggagttc tgtatctgca gacccttttc tcaggcacct 9300
gcctaactaa gatgtgagaa gtttgtgaaa ccctgctggt gtcacataac gtccctgtgt 9360
gagacgtagc tgctgtgctt aaatgaacta ggagaggttc ctgatattta tacagctcct 9420
ctctcaaact ccaaacctag aaaaccctga gaggtatggg agcctattat aatggtataa 9480
tttcctccaa tctcagtgga cccccggctc cagctctgag gagctggtga atggctggag 9540
catggagaaa gaagaaagag cctcactaga tattggagtg acccttgaaa atgactgtgt 9600
taagtgacta gaaacgcata gcccacagcc ctgcggaacc ctcttcaccc aatgcttgtg 9660
ggaagctgct tagcaccaga ctcctgggag aacaagtggg tgcagagagc ctctgctggc 9720
ctgtccccaa gccatggcac ttcccactgg ggatgtggcc ctcacgtgaa gccttttgct 9780
catggagtat gatcctaaca agccggtcac tataggcaac tctagagtct agagcaagtt 9840
agaagcaggg agagagccac acaattgact tttaaaaatt taattatttc tgtgtgtata 9900
tgtatcatgt gtgtggagag atcagaggac aagttgaagg ccttagttct agggctcaga 9960
ctcaggttgt ccagtctctg cagcaagtgt ctttgccccc tgagccatct cgccagccct 10020
cacttaatta tcttagccct ctgggctttg tgaaaaacgg gggggggggg cctattccat 10080
gcaacacctg gtcaaataag atcagcttag gtcctcaagg tcaaaggtct ggacttctta 10140
ggccccacca gcattcaagg agttccctcc cacctcagcc accaccaggg tctgtcacgt 10200
agtaggtaca tcagtaattg cagcttggta cctcaacata ggtaaggact gaagagcctg 10260
tgggggagtc ctagagtggc agcaccccgc ccccacacct ccttcccctc cttatttgga 10320
cagccctggc cacattttcc tcccttaccc aaccgtcacc atggtgagca tggctgttta 10380
tttaacagga caaacatttt cttcggattg cagcaggcag gccccaggga gttggctctt 10440

-continued

```
accaggaagt agaaaacatg ttataatatt tgaggttgta aaatactgtg gggttcgcag  10500
actcgaggta caggctgtcg gggccccctg ttatataaag ttgggaaaca gtcaggagtt  10560
tgctgggttg tgactagccg ggtgtaggct gttcttgccg gctggtcaga gggttcaggg  10620
acgcatacca aatggggatc ttacaatgtg tgcgtcttta ctattctctt aaggaagtag  10680
gttccttatt cttttccctc agaaaacgta ttcatttccc tcttaagcag gaggcggtga  10740
gggtgagagg accttatgtc tgaccctggt tggcagtgga agctggagcc ttgtcaggct  10800
ctgctgctgg tcctggacct gttttgtcat cgtggcttgc tgtgttttta accatttctt  10860
gtggaaagtg tagctagctg cagaggctga gagagcaata ctgtgaactc ccagcagcca  10920
gcctggggta ccctccccca ccccagaccc atgatctcat cacccagggc tcttttcctc  10980
tgtctggctg aggaaagcga acatggccaa gtgaccgggt caacaacccc agcttaaccc  11040
ctgccctcag gctggctact atccacggga gaggctagtg gctggatatg ggagcgagtg  11100
ggctcaggcc aggatggtct cagccaagtt ctccctttcc ctcccagacc cctccctgag  11160
actgtcccct gtctcccagg ggctcctgtc cacccatcag agctgggacc gagcgctaga  11220
ccataagtac aggaggcaaa gtctgcttgg accagcaaca gtttctgcca acttggcaaa  11280
ttgatgtcag tccattaagc tacttgtgtt gagcagtgca ttttctggaa taatgaggtt  11340
ctcagcgact tagtttagtt tgttgcctta cgtgtctgcc gtgtctgcct ggctctctct  11400
gtgaaaaagt gtatcttcct ctccaaagtg accctgttca catgggtgct cggggacggg  11460
aactgccggg cacagactat ccaggtagcc cccgggtggg gttgtgtgga atgggggggg  11520
gtgcatttta gtccttttca tgtaagccag agaggtgcta ccagctggct ccacagtgaa  11580
ctcccccacc ctaccccaat tactgtgtga cctgcctgtt tcccctgtcg tgacttagcc  11640
ccaagattga aagctggtat ttgtttgtca tttactggag tccagacaga tcagaccatt  11700
taatcttccc aagtgccaat aagagggagg ggcagttttt actcccatca tagaggtaag  11760
gaagcatggt acaaaaaaga tggctgctca tctgcctgtg gtagaggggc tggatgtggt  11820
ctagagtact aggatcagga tcaggagtaa tcaacccggg gggcttcgag aggactgggt  11880
ggccacactg aacctggagt caacccaagg gaactcaagt gacaagtctg tatcaagtgt  11940
gctgtacacc gagggctccc tgcaccttat cctccccacc agtcacaagt cctggcccac  12000
cccatccttt aagtctccca gggatttttc atatcctatg cattctagtt ccttgatgat  12060
catctgtgtt ctaggaggca agcctgaaag agcaggatac cacctgttct ccagtctgct  12120
agaaggccac cctagagatc cctggcacag tatttgcagg tgtgccctcg tgggtttagt  12180
gtttaggact ccccctatag cacttttcat agtgggagca caaaactgtg tgctgcagta  12240
tcctaggctc tactacccca gcccttccag taggtgcaca tgcacagaac tcttcggtag  12300
atagtactgg ctgtgctagc ctgtttcttc cagctggtac acagtcacct gtggtgcaga  12360
gtcttagact atgctattcc ctcccacacc caccccttacc ccttctaccc ccaccccctg  12420
tctcctggca ggtacacagt gctcttcagt gcagagtctc aggcatgtgc cttccatagt  12480
atgcactatg ccctgggagt ccagcaggaa acactcaaaa ctcctgctct ctaaagggga  12540
cggaaacacc atcctgacac aacccccaca gggagaggat gatgaagttc tctgggtagc  12600
taagaagagt gctgtgaccc agagggagtg agactatata cacaggctag atcgagagat  12660
gggtagatag aggtggacct agggacagct agacctcaaa gagccttcag tctctttttt  12720
agacaaagtc tgtcctccgg tcacagacct actataagtg acatatattc accagagtca  12780
cttgtcctac cgtgttgact gcggtggggc cgggtggagg cagtagcctg gtttggaagt  12840
```

-continued

```
tgaggctggc atctagccag aatgttcaca gtatatcggt atcatacaga gacgcccgcc  12900
ccaccctcta cctacagtac tgcttagttc tgttgttcca cagactaagt gctcaggact  12960
tgtgtagggg ggttgacatt tctgtgtctc agttcctaga aagaggaaag gtcacatgct  13020
cctttcagag agtctccgtg gcgacattcc taagctcctg gggccatcag tcctccacct  13080
ttaccatcac catacagtgg gtcctgctaa tgttcagtga ccagtggaca agacttcttt  13140
tgcattctcc ttgtgttgat ggtctgagtg tctctctatc gtttcctgta tctcaggggg  13200
aagcccctcc gtgaagcctg tgcttcagcg ttctcctaaa gtctcctttc ttccatcttt  13260
ccttaaaaaa aaaaaaaaaa aaaaaaaaaa aaggccaaac ttgcacattg tactctgact  13320
ttagctgaac aattcctgca tttggacttg ggatactgac aaactccctc tgtctggaac  13380
acagcaagcg agtccctgtc ttcccttccc cgtgtacttc ttccttacag aactgagtgt  13440
gagcagtgcc tcctggggcc cctgcctggc accccccttcc tactttgtag gtcacatgtt  13500
tggttttcct tgatggatac cagtaccgct ttcttcactc ttgaaaacat agttttaact  13560
ggggcttcta ggtttgtagt acatggtacc cagggtgtac acagatcggc agattcaagc  13620
ccgcccatct cggtgttctg aggctttttc cccccggcac gaaaatggcc actttcccat  13680
tggtctttct tcctcttagg taatgtcacc ttcttagaca ggtgtggtgt gtaacaagct  13740
gaggcaggag gattacaagt tcaagactgt tctgatctac atagaaagac tttattttac  13800
caaaaacagc aacaacagaa agtcactttc tcaggcatct ccccccgccc ccgtgaccaa  13860
agatacaaag atatttcttc ctttttgact gatatgtgtc tttttttttt ggttctgatg  13920
tcatgttttt tgtcttggcc tgtggcatta tctcagttct tgtcatttgt ttcatcaaac  13980
ctatctcctg tagactttct gtgcatgagg aagagtaggt accatctgtc catctgtcct  14040
gggttggtct tccctcactg ctgatggcag tgcttcttcg ttggagcctt gtcgaaggcc  14100
ccactttggc ttttgtttgt taattgtgga caaacagggc ctcatccctc atgacaagaa  14160
acatgttccc agaaacaacg tggctggctt ctgtgtggcc ctcatctcct tggagtcagt  14220
ccctcagtgg gtaagacctg ggcaggtcct agataaagga tcctgttggg ccttatggtg  14280
ccatcgtcag ggttttgaat ggatgtgggg cctgctttgt ttcctgccta tgtggccatt  14340
ttcttggtgt gagcctcaag ctgttctgcc ccagtctgtc tgctagagtc ttcccaatgg  14400
ctactgggaa gatgtcccac tgtcccacaa gtgggggtga tctgtagtgc ttggtcctct  14460
tccttagggc ctggaacagc tgggcagggt gtgagaccct agtgccgtcc ctggtacact  14520
atttattgtt cccgtaactg gtggcaaaca gttgaaaccc ttggagcttt cctgggctgc  14580
agaaaaccac actgtttcac cagcagtttt aaatccttgg tcgtttcaca tgaatgaggg  14640
aagaatggga tggagggctg tctaaaaggc atccctgtcc ttgtccactg tgggaagggt  14700
gagcacatgc tgcagacagg cagtgccatg gtgggccatg tcatcacaga gaagcctcta  14760
agcttagcat ggatacagga cccaccagag catcctgggt caggccagtg tggagctggc  14820
tgttattcaa ccttatgcag ccctgggtga gtgtcctacc ccatcacctc ggcggcggca  14880
tggaatcctt catgcagcgc ttgcggtggt tgtagtgtga cctgcgctat gtgtgtcagc  14940
cttccattga caactggtgt tttcctgact gcaaggaacc ctgtggggggt attgtgcctt  15000
ttaggatgct ctcagagaac ctactgctga cacttggcct cctagcaagg gccagcaagc  15060
cccctgtcct ccaacttcct catgtgcttg gcagagtaga ggtcagaaga agagagcagc  15120
caggcgtgtc ttccttggcc tgctgtggtc cgggtttcct cagctccttc ttcttcccta  15180
```

-continued

```
ccaccttggg ctgtggcgaa ctctcccagg cccagtctta acagcttgta gctgtttgca  15240

taaacttaat gtgacccgac tcagcttaag tgacatctgc ttccttccag ggtccctggc  15300

cctccctttt cctcccagcg acatctaaca gtctcttacc cttgagttat ggcctcctat  15360

ctggtgatat gcccaccctt ccccatcact aagtctgtga tcttttatgg ggttcagagt  15420

tctgtggaag ccttcttagc ggtgggatgt tagctgtttc tgcccaccta tccctaagca  15480

cacaggtttc tatttagtgt ggccatggga tccgacccaa tgtaaaccac gccatgactt  15540

tgatgcttag gcacttcagg ggcccctgac gactcagggt aagcttgagt ctccttcccg  15600

cttacaccat cttattccaa tgccaggctc cctgcagcgc cggagcccct agcacctgga  15660

gcgctccatg gcatagaggc ctcttcaccc ctcacccaac agcattacct ctccaggaga  15720

cccggctgcc cccagcttct ctgtagcaca tgccatgttg tgatggagtt gtttttggac  15780

cccactgctt aatgtcacct gtggagataa taggatgaag attctcatgc ctggtttacc  15840

atttagcatg gctatatttt ccccactgtc atgtagggtg gctgtctgtg cccttgtctg  15900

tccactggta agtctgtcag cacctccata gcccagctga ggctctcggg ccagctgccc  15960

tcctgatcca gggccagtag gagctcagga atcaagaaca cataaacact acagtaaatg  16020

gcagctgtgc tgccactgat actgggaatc aaaccaaggg cctcgcacag acaaggcgag  16080

tgctttacca tcgatctcta gccccagcct ctctggtgcc tttgaacgtt tgcccaaaga  16140

tcttctcctt ccaccagctt attccagagc ccgacatgaa tggatacgtg gacttctccc  16200

caagtcccac cagtcccacc aaggagccag gggcacctca gcccacccag gctgtgctcc  16260

aggaagacgt ggacatgagc agtggctcca gcggaaacga gaactgctcc acgggacggg  16320

actctcaggg cagtgactgc gacgacaatg ggaaggagct gcggatgctc gtggaatctt  16380

ccaacactca ccccaggtag gtcagcctca ggccaggccc tcgcacacag gacacgggtg  16440

gctccctcca tagtttgtcg cccgtcttca agcagcaagt accaggactt gcaggatggc  16500

agtacttctt aatcctgtag atggtattta ttgtactttg tccttccaaa taacgatacc  16560

acgtcatctt tgcatttttg tatctgatgc acttaacaga cagtccagta agacctcgga  16620

ggagcctgct cacacacatg cattcggtca cagaatattc cttttcattt ctgactctca  16680

gtgttcaagt ctcctaatag ctgaagctct tatgtttcag ttttaacatg acttttcctt  16740

tcttaaattg ttactttaaa gtatatgggt gttttgcctg tatgtatgtc ggtgcaccac  16800

ttgcatgtgt ggtgaccata cgggacagaa gagggcattg gatcccctgg aactgtgagt  16860

tacagatggg tgtaagcagc cgtgtgggtg cttctcttca ccattgatct gattctccag  16920

ctctgacttt tattttgagg ggaagtatgg acgccatact atgggtctaa ggcactccat  16980

gcaaagtcct ttgtgccaaa gcca                                         17004
```

<210> SEQ ID NO 2
<211> LENGTH: 17112
<212> TYPE: DNA
<213> ORGANISM: Homo sapiens

<400> SEQUENCE: 2

```
caggatcagg gaccctaatg acagcaggcc ttgttggtcc ccagagcatg caaggccccc     60

gttcctgact ccaagatgtc catggttgga ggtgccaact gggctacccc tcagtgacgc    120

ccccaggaat gctggcagaa ccacactgag gcaacagcct tgcaggacgc acactagaca    180

gagagggaca gagccaggga gcctgctgca ggggcctgcc cgggtaaggt ccgtggccca    240

gaaggccagc aggatgacac cctgaccgat gagagaccct ccacctggga aggaagagat    300
```

-continued

```
gcctcggacg tggaggatca ccttgaacac gggtatcacc tcagacaggg ggcatcacct    360
tgggtgtggg ggggatcagc tcagacaggg caggcatttt tgacaagtta cctctccttg    420
ggctccttca ggacagtgag gggtactggc tgcccagaag ccctggaaag aaactcaagc    480
tgcctgagac cagaaaacct gatccacaga ttagtccaca agttcctgag gcagagagtt    540
gacctgcaac tcaaaccagg agcgccatac agcatcacct acccactgct accccctccc    600
caccaaaggg cacagctttc gtctcagtga aatccttggt tttctttct tttttttctt    660
tttctttctt tttttttttt ttgagacaga gtcttgctgt gtcacccagg ctgaagtaca    720
gtggcatgat cttggctcac tgcagcctct gcctcctggg ttccagcaat tctcctgcct    780
tagcctcccg agtagctggg attatagaca tgtgccacca cgcccggcta atttttgtat    840
ttttagtaga gacggagttt caccatgttg gccaggctgg tctcgaactc ctgacctcag    900
gtgatctgcc tgcctcagcc tcccaagtcc ttggtttttc ttaatggcct taatgaccag    960
aaagtttgag gttttaatcc tttctcaagt gacatgatag caaatttttt cttggctttg   1020
gttaaaagca tgccttttat ttgcaaaact gataataaga gaagtcagtt gggtacacat   1080
ttaatcactg aattcctgta gcaataaaga ggatatgtat aacattaaaa agacagaatc   1140
ttcaggtact aattatttta ttcatttata ttttttgtct taggatacaa taatgaagta   1200
aacaagtcta tacagagtat tgtatagcag agacaaagct atggcaattt aaattatttg   1260
cagatctgca aaaaagaaaa gattagatgt attttggaga ggtatttttg aagtaataac   1320
tattgccatg gattaaaagc ccactgcacc tatgtatgat gaaaaaaaaa aagcaaaaca   1380
aggctgggag gggtgtctca catctgtaat cccagcactt tgggaggccg aggcgggcgg   1440
atcacgaggt caggagttcg agaccagcct gaccaacatg atgaaaccct gtctctgctg   1500
aaaatacaaa aattagctgg gtgtggttac gtgcgcctgt aatccaagct actcaggagg   1560
ctgaggcagg agaatctctt gaacccagga agcggaggtt gcagtgagcc gagatcatgc   1620
cactgcactc cagtctgggc gaaagagtga gactctgtct taaaaaaaaa aaaaaagaga   1680
aagaaaaaga aaaacaaaca aaaatcttag cgaattagaa tatatggcaa tggacatcta   1740
taaaaaagaa aaacaaaaat cttagcgaat tagaatatat ggcaatggac atttataaaa   1800
aaacaaacat ctaaggctca tcatacctgg tggtgaaata ctgaacactt cctcccccag   1860
ggtggaacgg gccaaggatg cccactctca ccattctatt ccacatcaaa tgcgggtcct   1920
agcttgtgcc accagctctg tgatctctag ggcatccttt gcaaaggagc cattgggaca   1980
tggatgctta cattccaggc tccaagcaag ctcctttccc caggctcttc tccagggtga   2040
ggcgaagaaa gatggggact gcacacccat cgtggatggc tcaatcttgt gacttccttg   2100
gggaagacat atgagaacac gtgtgtgcac atcacaccca catgtctccc ctaaacaaag   2160
aacagcctcc ctggatctat atttagttta aaaatcaaaa agccttctca gtaggtagct   2220
agcatgataa agatgccttc ttcttttttt gaaaagatag gatctcagtc ttgctctgtt   2280
gcccagcctg gagtgcagtg atgcaatcac agttcactgc aacctcgaac tcctggcctc   2340
aagggatcct cctgcctcag cctcccaagt ggctgggacc acaggaacat gccatcatgc   2400
ctggctttct tgtttttttgt agagacagtg tctcactatg ttgcccaggc tgttctcaaa   2460
ctcctgggtt caagaaatcc tcccaccttg gcctcccaaa gagctggaag atactttctt   2520
tataccggtc cgcaaaccac ctcatgtcca gggacaggca cctgccctcg ggtcactaga   2580
ggcaagttgt ccttgtctca ccctgagacc ctggacacag gtgcccgcgc ccttgaggtc   2640
```

-continued

```
acctctgtga gctggctgag ggtctccctg ccaggagctg ccaccatgcc aagctggggt   2700
cagccgtagg tcagcgctgg gttcaaggga ggctggagag taagggttgg gcattatcat   2760
ctccaatgtc cctaggccca agaaagggc tccagcacta gggggccaga aagcttgaca   2820
gtgtcccctc catctcttta gagagacttt gctggccacc acctcctcca tttgcagagg   2880
gaattctctt cctagccgcc tgtcctttgg ccctccagct agccaacccg caaaccatgc   2940
cacctacaat gagaggaagc agtgatcagc acagttgcct ggtacatagt agttgctcag   3000
taaacaattg gctgggtgca tgagtgaatg agagggccag tgagtggact ggcaagggca   3060
tggaggcctg ggtgcagaga ggccctacag gcaggcccag acatagatgg gtgggccaac   3120
ttgggccagg cttactggtg gaaacaggct ggtgggagtg ggtggagcag gggccaagca   3180
gcctttagct gggaggccag ctcctcccac tggcagcatt cccaaggtag gtggggaccc   3240
tggcttacca ctccacctcc acccccaact aaaggactag ctgtctccta gccagcctgc   3300
ctcccacagt gccaacagca attcccctat ccaagagctc tgagctccgt gctggaggtg   3360
acagctggcc agtgtgggct ggctaggaaa gggttcatcc cccttccttc tccaatctga   3420
ctgccccaat ttgcgctctc tctctgtcac catcttggtt cagcaagaat ggcatccatg   3480
cacttggcct gattgtagga gctcatcccc tgagcgctgt cctctgttgg agctgggatg   3540
gaggcttctg tccatggctg tcctattccc tcaggaccta cacaccacaa cttagacaaa   3600
attgcctctg aatctgcctc ctcccccctt ctacatcacc aactccttac aagcagggat   3660
gcagtgagat gtatttttgc atgcccctca acactcaggt gtcaacaagt atttgtggag   3720
tgtacacaaa tttccaataa taggaaagaa gaaactggct gtgaatcact gaaaatagat   3780
gagattctga agagtcctag agcccaaagc acttgataat ttctaaaaga attgatttca   3840
atatatttct accagattta ttggtggaaa taaaaaaggc tacatttagg gaggaaatgt   3900
gacatcaggt agcaggctga atatggagca agacccagca aaagcatgaa gaagaatctc   3960
ggtaaggtgt ggatgagctg tctgtttact cttgtttcca gaacaatgga gctccccatt   4020
gacgtcaatg ggagggaaga aacaaaagag cctttgggtg tgtgcagggc gcagcagccg   4080
ggcctgggtt tgcttggcat ttgtgtgtgt atgtgttagg gagagggggc ggggagtgtg   4140
tcgaggtgtc aatgtcagag gaacaggagg aggggccacc tgactgagtg tgtgaacagc   4200
atgcaggcct cccggggctt ctgtgggaag ggctgccccg atgaacttgg tatttgccct   4260
ggtttgcatc tgagaagttg cacacacacc ttgtcaagta gaagagaagg agttatcaca   4320
ctcaggaatt cctgatgtgg gttcataact tttccttctg tcccatccct ggtccccagg   4380
tgagtccagg taaagaagaa caagaagagt aaagagagat gctgcgggct ccagcttctt   4440
ggacagtctc gccttcccca tgagagccta cacattcaga gcctgctgcg tgggagcctg   4500
aaagctcctt cctgtcctgt aagtctcagg cttctaccca gacccgggga aattgtactc   4560
tttctcctga cactttaaat ggaagtttag aggctccaca tgccccacac aatgcttacc   4620
gaaacaaggt gatgcagggt cccgcgctgt ctcccaggac aacctcctac ccctggctcc   4680
tgcgtctcta cggcttgcac cgttgtaagg cgtccctttc tcagggccca tcttacccgc   4740
cttggaagtg ctgcctttct cacggagcct gtggggatag ctctggttaa tttatagccc   4800
acatcgccca atttagcatt tgattaagtt tcctttttat gagatagtcc tttctcccta   4860
gtgatgcgct tgggggcagg gacaacatca tttctttctt ttgtacctcc ccagagtaac   4920
aatgactcta tttcctgaac caaaaattgc aacacgtggt ctcaaaaata agaaaggtca   4980
cttggtagct gccgggacaa gtgtcgacca caggcacctc agaggcccgg gtgggcgtgc   5040
```

-continued

```
ccccggagct gctgcagggc ggtgctgcca ccttctcctg ggctgctccg gggccccgcg   5100
atgaatgagt gagtgaatga gtaaatgaat gaatgtgaat gcgtgaatga agcatgccgc   5160
gcggactttc ccgcggccct ggccgctggg ggcgcgcctc tggccggtgg ccggaggtgg   5220
aggtctccct cgtccggctt cggcgcgccg ggtctgccag gccggccgga ggtgcgcagg   5280
agccccgcgc ccagctcccc cgcccgcaat ggtacgcgcc actccgcgct ccccgagctg   5340
gcgggcttga gggcgtagtg aatggaaggc gccgacgccg gaagtggatg agaccactag   5400
ggaggacgac gggtagcacg aacgcgccgc gtctccattg aggaaccgac gaggtgaaca   5460
tggagttcca tgtgcgtctt atgtaaaaag agcgacgggc gcggccacca atgggcgcgc   5520
ggcgttcgta ggccccgccc ctcatgtatg cagatgagac ggagtcgcgg ccaatggcgg   5580
aggccggggg cgggcgcggc gcgcgcggtc acgttttcca ctatgtgaca gcggcgactc   5640
ggccgcggcg gaggcggcgg cgctgagggg atacgtgcag ctgtgggcgg cggcggcggg   5700
cgcggggccg ggcggacaga gccgcgagtc ggcggaggga ccggcggacg ggctgacgcg   5760
ggcgcggccg gcggtaagtg gcgcggcgcg gccccgctgc ggcttacgta accgccgccg   5820
gcgcgcgggc ctcgggcagg tcggggtccc agcgccggct cgggcagcgg aggcgccgcc   5880
ggaagttcct tgggctgctg gactcctcgg cttgaaacgg cgccggcgtg ggggcgtgtg   5940
cccttggccc tgtcccaggt ggagagtggt cgagccgcgc gcagggtgcg ctcgtttgaa   6000
ctgcggtgac accgagggtt ggggactcga accccccgctt cgcagctcag gagcctgagg   6060
tccgaaaggt gaggcagcgt gtgtagggca ccgagctacc gagtgactgc gcgcgggctg   6120
cggttccgtg ggcgattctc ttttgggaac cctccctccc ctcgcatggg gaaggccaag   6180
gaaaccaagg gtcagcgcag ccggccctgg gatctggagg accctcgggg agctgactgc   6240
ctcttctgag gccacagggc taagtcctgg gctggggaag ggccatggag ggcgctgat   6300
ctaggagctt ttcctggaca cccacgggtc tcctggaatg ggtgatcaga gggacaagga   6360
agtcccggtg ccaagccagg cctgggaacc tgagggcggg gagaccctct aatgttcgcc   6420
cctttgcctc ccctggacca ccctgtatta attccctttc cccggactgg atagaaggga   6480
atgggggtgt ccactctttg gtgcagcagt cgcgcctacc ttctgggatg tactttggct   6540
gccaagtccc agacatagac caggggggtgg gaggtggcct gcttcccccct tcaggaaggc   6600
cagggtaagg gatgacgagt tggttgccag ggtttctgta acctacacag aaggaacccg   6660
tttggaaagc tgattcatac agaacaacag agccagaagg caccctgaaa atcacccaga   6720
gtaacccctc agcctgacag atgagcaaac tgaggcccag gcccaggctg tctgcaggat   6780
cttcccatcg tcctggggca ggatgagctt cagaggttca gtgatggcct ccacttgcgt   6840
gctgaatcct gggtgggctg gaatttggga ggaagggcct taagtccggg aaatgtgtta   6900
agaaccccac acggtggcta aagccccaca tggacgcctc tcacctgtat atggcacagc   6960
aggactgcta gacttcttgg cccaccctct acccccacct ggggcttctg gtcccaggct   7020
gggtgtgcct gagaagaaaa caggactcta cctgaaggct ttatttggaa attgagtttt   7080
aaaatacaag gtgaattgat ttttgtgtgc tatatgacta taatgaagaa agggactccg   7140
tttttttga gtggaagctg tgtggtgtgc cagcgcgggg atggcaccgt gggtgtttgc   7200
agttatctgt cactgtcgcc ttggtatgat tcattggtac agaactaacg cagccctggc   7260
tttctgtgga gactggagtg ccaggtggga agggggagcc ctgtgtcagc cagctggctg   7320
ctgctggctc ccagtctggg cctcagtttc cttgtttgtt tggaggggct cagattgggc   7380
```

-continued agtctcagag gtctacttta attcccaggt ttttggtttt ctgttaccct acagatgatt 7440
tttcccaggt ttctcgcagg agacagaggc ttctgatatg ctcttgcctt tgggccaagt 7500
aatgttctcc tgtgagccac gtctgcagtg cttacaagga aaaaggaaag attcctctcc 7560
tgtgcactac ttctcgtacc cactgaactt tctcaaaaat actggtagtc acactgctgt 7620
ttttaagcga tgatgtaact tcaccaggac tcggcaaacc acggctctgt caggtcattg 7680
aacagctggc agggccactt ggcgtttagt cagaagaaag acaggctctg ggtgtgcttt 7740
taccttttga aaactactct gtttggcaga gggagccaga aacacacaat tccataagct 7800
tggcagagac tgtcgccaca cttctggaaa gctggcccac cttgggaacc aagggagaat 7860
tagtctagag gggcctctg atggacccct cccccagccc acgcactccc ccctagggac 7920
caggccctcc tttcaactca ttatgctcat cgtgtacaca tttgtaacaa gtttgttacc 7980
atatctccaa gtctagagca aattagaagc agtaaatgaa tagcagtgac tggtgacagg 8040
agtcaaggcc acttggtttt cagagactgg tagttcccaa gacagagtga gctgccgtgc 8100
tgaaccctca ccggcctcga agggttcctc gtgctcttcc tggggtgaca tagaggaatc 8160
agaatccact ctttaagaaa ccaggtacag gaggagcaga tgcctgagct tcctgcaatt 8220
cggagtagct cagtccctga ccaccgggga gctaggaggc tgacactttt gcctttattt 8280
gctttaaagt cttgtagttc taaaaatgta gggatttaaa agtctgaatt gagatcattg 8340
aaggtgtcct agtgaggcca agacaatgcc tccccggtgc acctccttcc ctccatattt 8400
ggatggctgc ggtcacattt tcctcagtta cccaaccgtt gccatggaga gtgcggctgt 8460
ttatttagca ggacaaacat tttctcagga ttacagcagg ctggcctcag ggagttggct 8520
cctaccagga agtagaaaac atgttagaat atttggggtt gtaaaatcct gcagggcttg 8580
cagagacagt acatgctgta tgagccctat tatgtaaagt tcgaaaacag gcagaattca 8640
ctaggctgca agaagccaag ctagtgagtc cccgcggggt agatggtggc tgggagggcc 8700
accaggagcc tctgggggc tggcactgtc ctgcctctgg tgacatgtga catggcatgt 8760
tgtttgtgga tatacatcaa gctgtgacct catgaggtgg gactcctctg gtgattgaac 8820
actgatttct gatttccaca aaaaatgctt ttccgcctta ggtttgcagg tattgagtac 8880
agtaagactt taccagtcct ggcagtggca gtggaggctg gaactgggtc ccaggcttgc 8940
tttcgttcct aatttttaaa cactattatg gaaagtatga gtatctctga aagtggggag 9000
gatagggtaa cgaacccatg cgaccccacc agccagtagt ctctgctcct ggccccactc 9060
cttccccacc cccaccagct gcttttcctc ctgatcccag gctctctgtt cttgtggtgg 9120
actgcacttt ctgaatggtg ctctgtcaag ttgaggcaac ccagctacca aaaatgtggc 9180
caggtgacct ggtcaggggt ccgagcttaa cctctttctt tgagtctgac tgttcttagg 9240
ggcagagcca gtaggcggac atgcaaagag ggcctcaagg gcaggttcac gcccagaggc 9300
tcatgttggc ttttggcagc cccttttcaa ccaggctgcc attttccctc ctgggctttg 9360
gtaccctgag cacataagtg catgcccacc ctccctcccc ctacccgcct tgaggtggaa 9420
acaggtttcc taggagctcc ccaggaacag ctggtccagc tggctatggg cacacatctg 9480
tggagggcag gaggcaaagt ccactttgac agggacgttg gttttgccag cttctcaaaa 9540
tgaggctggt ctattagagc cgctgaggct gagagacgca ttttctggaa tgacgaagtt 9600
tctgataatt tggctttcac atttctgcca agcttactct accctctttg caaaaatact 9660
tatcttccac ctaaggtaat gtcggggcac cagtgaatcg tatttagaca ggcttacagg 9720
ggatggactt aggggtgaaa accaggagag ctacgtgcaa agcacccggg gcccagacag 9780

-continued

```
catggtggct tcagatacct gatgctcctc taaggactgc ctgggctgga ggtggcactg   9840
agttcttagt cctttaaata taagaataca agccagagac agctgccatg acaattcatt   9900
ctctctcttc caaaattacg tttgttgccc atctgttttt ctttttcgtt ttctctctct   9960
tttttttttt tttttgagat agagtcttgc tctgttgccc aggttggagt gcagtggtgc  10020
aatcttggct tactgcagcc tccacctcct gggttcaagc aattctcctg tctcagcctc  10080
ccaggtagct gggactacag gcacacacca tgacgcctgg ctaatttttg tatttttagt  10140
agagacgggt ttcaccatat tggtctggct ggttgcgaac tcctgacctc gggtgatcca  10200
ccgcctcagc ctcccaaaat gctgggatta caggtgtgag ccaccgcgcc cagccgccgt  10260
ctgtttttct gtagtgatta gcagtgataa gctaatatta cattccagat atcttgcatg  10320
ggttgtgtca tttaatcctt ctaacaacca gtaggaggca ggaactactg ttaccccatc  10380
tcacaaatga ggacacaagg ctcagggagg ttaaggaact tgtccgagat cacataggag  10440
gtggtggaac ccagctgaaa cccaggccac ccaggacctg tgcccttaac cactctgctg  10500
ctgcctctga tcaccttaat gactcactca gagcagaaag gaccagctgc ttatctgggg  10560
gagggctgtg ggatgagat gggtggtgtc cagggtgttg aggggtcagg agtgagagaa  10620
tgcccttggt accctgggcg gccccttggc agctccactg aaccatggca agagcaccct  10680
gagaggtctc cttgcttcca ccttgcctca accctgcaac tccattgaag tgtaagtgag  10740
atcttgttgc acagaactct ccacagttcc ctatcggagt tctgactgcc cccgcaaggc  10800
actccgtgat ctggccttgc tgccgccctc ctaccgctgc ccgctctgct ccagcctcgt  10860
gcaccttcct cagacaggtc aggtgcttgc ctgccgcagg gcctttgtgt gtgctgtccc  10920
cctgcctaga atgttcttcc tctggtagct cactctccac tctcttcagg tctgccttca  10980
ggctctcttg agaatggagt ctgaggtgag cactttactg ggaattgcag tcccagggta  11040
gcagtagaaa aggaaaaggg aggtaaggaa gaaaagtctg gaaagcacac acaagacgac  11100
accctgctga gatgaggctc tgccttacag agacatccag ctgggtgctc accccccttgg  11160
gacctcttca gaaaggctgt gccaaaacag gaaggaagga aagaaagaca acttcagaaa  11220
ggtccatttg agggagagag ggagggggca ttttctgcca gctcctcctt gcctcctgtc  11280
cagcaagcga gctctccctc ctatccagct gcctcatcag accctttggc agcaggcagg  11340
acagtgagga gcagcaaggg cccccacagt ggtgtggcac gtcatccgag tccacacagg  11400
gcaggcagag ccagagatgc ccagtgccag cctcaggtgt gaagccagaa agacctgctg  11460
aagcacgtgg ctgcaagcct gagagagcga agcccaggga ccctgagtca gttcacacac  11520
gagggctcgt gcgcaaggtc cttgtcaaat gccacctaca cctggggcca ccctcattga  11580
aatgtcactc ccagcccctc aattcccact tgctagttgc ctactctact gtatattcta  11640
gtttcttgtt tattgtctgt ttccccctaa tgtaagctcc ctgagggcag gaaagatgtc  11700
tgctctgttg tctgccccag tgccagccct cagtgctaag cgaataaggg caagtcagtc  11760
agtgggaaac tgctggcacc gggcaggccc tgcctgagtg ccatctgtcc tttttattgt  11820
tgttgttatt tattgttctt ggacttgttc atctatgtct gagactctcc ccacatcagt  11880
ctttctggcc tctatccttt tagtgggtgt atagtattca tagtatggat gtcccaggtt  11940
tgtgtcttca acagtacgtg ccaggccctg gggatccagc attgaccaac gcaaacccct  12000
gcccccatgg agcttaggtc ccagagggga ggcaggcagt aaacagccca gcccctcagt  12060
gctggcgagg aaagcccaca gagcggcggt ggaggcacag agaaggagct ggtggggaga  12120
```

-continued

```
cggtgctgtt catgcaggct gcccaggcat ctgcaagaag agggctgtgg gcacgaggga  12180
gcagcaagtg cagagtctct gtggtcagag cacacagggc tggggctgag ggtgggcag  12240
ttaacaggac atgcccagga gattgcagga gctagacttg cagagccttt ggcccttgtg  12300
cacactagaa ttgtgctctg agcaagggtc tgagcacggg ccgggcgtaa gctaagcccc  12360
ttcaccagga tcgctctaga tgctgtgtta accatagcag ggccaggtgg aggcagggga  12420
ccagtctgga attggaggct ggctcctggc caggatgatc gtggacagga tgcgtagcct  12480
ccctgttgat ggttcttccc aggtttttat attcagtgct cacacatctc tgagcacata  12540
aataagcact tctctgcaat ggattcctgg aggtgggaag agtatgcaga ttataaatgt  12600
tgctgggaac tcaaatttct ctccagaaat accctattac tacaccacca cacacaagag  12660
ccactcttct ccacctgagc aacgctgagt gtgatcagtc ctgttaattt ttggcaacct  12720
gatgggcaag ataacctcgt cctttgcatt ttcctgatgc taatgaggtt gagcctcttt  12780
ctacaagttc acaaatcttt tggtgtctct ctttgtggga atggcctagg cagtcttctt  12840
gcttagtctc tctgttccca aaaggtatta ccattcatct ttcattgaat ttgctagaac  12900
tgccattaaa tgtaaaataa agaaaaaaga ctagaataac agatttgctt attttgttcc  12960
tgactttaag gggaatgatg ctggcatttt gggttttatg tgactcagga tgttgataaa  13020
accagctatg taacccacaa tcaagtatcc tgtaattgag atttcctccc tttgaccata  13080
agcttttcct ctcaaagcta ttaatatatg tagacggccg ggcctggtgg ctcacgcctg  13140
taatcccagc actttgggag gccgaggtgg gcagatcacg aggtcaagag atcaagacca  13200
tcctggccag catggtgaaa ccccatctct actaaaaata caaaaattag ctgggcgtgg  13260
tggcggacac ctgtaatccc agctacttgg gaggctgagg caggagaatt gcttgaaccc  13320
aggaggcgga ggttgccatg agccgagatt gcgccactgc actccagcct ggtgacagag  13380
caagactccc tctcaaaaaa aaaaaaaaaa gtgtaaacat tgtcttctgg aaatgtaata  13440
ttgctgaaga gatatccaag actagtgtga tttttttttc atcctttatg ggtaacttgt  13500
ttgttctctg tggatgttgg taggactttc tttatccttg aagataccgt ttgtcatctg  13560
gatgcactta ggcgttggac tcttgtcctt tgattggcag attcagatct gtctctggtt  13620
caggatggtt ctctttatgt gtctcgctca ttatggtttc tgttttattg ttctcgtctc  13680
tttcagaaag agctgtaatc cacaggtaaa acccggctgt cctccatctc tcttctcttc  13740
tcctttccct ttgcatttta aaagtctgtc acgcatctcc tatcactgaa gccattttct  13800
ttttattgat tctgaacttt gtcctttcta gttttccatt ctaatgtggc attttcatct  13860
cagtcagtgg ccttatctca tccctcatta cttgtttcat tgaatccatc atttcttgaa  13920
ttcttaggat gaaaagtaga tggtgtctta atttgctgct tcctctgtgg catgagggtt  13980
gtgttcagtt gtctttgctg tgtgtgtttt ccacagcccc gtgttggctt tcttctgttt  14040
attagtttgt gaacaaggcg aggtctagtc ggccctgctg ttctccagac actgatgtgg  14100
gtggattctc catgagcccc gcctctcacc aggctgtcct ggagtggctc accggcgaat  14160
gggctcgacc tggggaaggg gatgctgaag gctcttgttg gagcttagcc attcagttcc  14220
tggggccagc tgttggaatc cggcaccctg tatgtgtagc cctcagtatt gctggctggt  14280
ttctagccct ttcttagagt tgccctgttg gggagggcac ctgggggtgt tcagtgggtg  14340
aagcgtctcc aggagaacct ctccttccca caggatttct gttcctgtgt ccgttcttct  14400
cccacagctt cctcacgaag catcttcctg gtggtagagc tcttgactgt ccagccttgg  14460
ccatggcttg ggccttccat ggccgggggt agcagggatc tcagcactag ccacttcctc  14520
```

-continued aggggtattt ggactccagt gcactcttca tgctccttcc atctcagcga caagcagccg 14580
gacgcacctt cactttgtgg caaatgattg ggacccttcg ggacttctag ggctgctgaa 14640
aatgatccct ccccccgacc aattgtatga tccttggtca tttcacgtgg gtactggtgg 14700
gaaggaggtg gaaggggagg ctctcccaga gctagatggg aactggagca taagatgttt 14760
cacaagattt ggggtgtgga atccagaaac ccttctctcc ctttgttcca gctgccctgg 14820
gaagggccaa acggatgcca tgcagaagtg gaatgccaca ctgggccaga gttggggctg 14880
agcacagtgc agtggcagga agcaggaggc ccccacacag ctgagcctgg gtgtagggtg 14940
ggggtcccat cttcagatgc cggcaggcct ggaatccagg gctgtcatct gctactgtgt 15000
ggcctggggt gagctaccca cccctgttgg ctgctccgta gaacgatctc ctgcgcacca 15060
tgtagaccgt gatccagagt tgctgggaag ctgtgtgttg ggtgcttagc atcatgtctg 15120
tagtcagcag catcacccca gagcctcaca gctgtgttca ttaagcatga ccacttgtgt 15180
caagcagggc cttcatctgg ctctctccag tgccccgctt gagtgggtgc ctgcttcctg 15240
ctgggactct gctgaaaacg ctgtcctggg gatggggaga catcactggg tgaagaaggg 15300
aggacccggg atggcatttt ggcctctcac ctgctaatca gtcccacccc tccctactcc 15360
ctgtctctgt tcaccccccc tcagtttgtg tccaggatga tcgctggtct gtctctaatt 15420
tcagccactc cacccaccta ccccaaagtg cagaggttaa gtttctgacc agcacagcag 15480
tgcaagcctg tccaaatgca agctgagttc cgtgggcctg gcactcagag tgcctcagca 15540
gctcccaacc attcccagta aatgtgaagc cacattgtcc tggcccctct ccatccccact 15600
tgtacatgct tgtggggcct gggatccccg agctgctggg agggttccac acctgccagg 15660
cccctctgcc ctctttaccc ggcaagccct gtctgtcccc atgtctcctg ctagccttgg 15720
ctcctcctcc tgtaactgtg ccgtgctgta atggccaaga tttctgaacc cggctccccc 15780
accccaccat catctgggga aatttataaa aggcagatca cctattcaga gggaccatgt 15840
gtttttccca gcaccccaca ggccgggtgt tgattatcag tgctcttgtc tgccttctga 15900
tgaggccgtc agcagctcta tgtcgggctg aggctgcctc attcaaccat cttcctaatc 15960
catggcagat aggagctctt gtcaataaga acaaataagt aatgtgatga actaacgtgc 16020
gtgtgattga tcccgatgaa agggcagttt tggctgcgtg tggttggcct gtaatctcaa 16080
cattttggga ggctgaggcg ggcagatcgc ttgacttcag gagttcgaga ccagtctggg 16140
caacatggca aaaccctgtc tctaccaaaa atacaaaaaa ttaaccaggc atggtggtga 16200
gtgcctgtgg ttccagctac cctggaggct gaggtgggag gatcgcttga gcccaggcac 16260
tgcattccct gggcaacaga gccagaccct gtctccaaag tagaaagaaa gaaagagaga 16320
gagagagaga cagagagaag aaagaaagag actgcagttt cattagtaac agaaagagtc 16380
aaatgggtgc tctacctgat ggctgcagcg ccccttgtgc gtgtgcttgt taatgcgtga 16440
cagcatccct ctgtttgcca gcttcgttcc agagcccagc atgaatggat acgcggaatt 16500
tccgcccagc cccagtaacc ccaccaagga gcccgtggag ccccagccca gccaggtccc 16560
actgcaggaa gatgtggaca tgagcagtgg ctccagtgga catgagacca acgaaaactg 16620
ctccacgggg cgggactcgc agggcagtga ctgtgacgac agtgggaagg agctggggat 16680
gctggtggag ccaccggatg cccgccagag gtgagttcag cctctggcca gatggaggct 16740
gggcaggttg ttttctcagt ggctcatttc tgctgtgatt tgattgcttt tgcaatcttt 16800
aaatcatgat taccaagttt ttcaagattt ttgaaaatac ctaaaatgtg ccagtgtctg 16860

-continued

```
tccttcctca taacgaggcc ctgtcgagtt cgcagatcca gttgccaaca gacaggtact  16920

gggtagtgta aggagatctt gggaggtagc agtggtgggt aacccagcca gtggctgctt  16980

atacaacact gggcagttta tagaaaagga actggctcct gttatcatgt gtttctgtgt  17040

cctggtactt agtttttctg atgtctgaag gttttatatt ccagttttat cttaaccttg  17100

tatttttaaa aa                                                      17112


<210> SEQ ID NO 3
<211> LENGTH: 22
<212> TYPE: DNA
<213> ORGANISM: Mus sp.

<400> SEQUENCE: 3

aggctgtgct ccaggaagac gt                                              22


<210> SEQ ID NO 4
<211> LENGTH: 22
<212> TYPE: DNA
<213> ORGANISM: Mus sp.

<400> SEQUENCE: 4

cacagcaaac atatccgcgt tc                                              22


<210> SEQ ID NO 5
<211> LENGTH: 30
<212> TYPE: DNA
<213> ORGANISM: Mus sp.

<400> SEQUENCE: 5

gactctctga aaggagcatg tgacctttcc                                      30


<210> SEQ ID NO 6
<211> LENGTH: 30
<212> TYPE: DNA
<213> ORGANISM: Mus sp.

<400> SEQUENCE: 6

gactctgcac tgaagagcac tgtgtacctg                                      30


<210> SEQ ID NO 7
<211> LENGTH: 30
<212> TYPE: DNA
<213> ORGANISM: Mus sp.

<400> SEQUENCE: 7

ccagaccttt gaccttgagg acctaagctg                                      30


<210> SEQ ID NO 8
<211> LENGTH: 30
<212> TYPE: DNA
<213> ORGANISM: Mus sp.

<400> SEQUENCE: 8

caaagcccag agagctaaga taattaagtg                                      30


<210> SEQ ID NO 9
<211> LENGTH: 30
<212> TYPE: DNA
<213> ORGANISM: Mus sp.

<400> SEQUENCE: 9

atttaagcac agcagctacg tctcacacag                                      30
```

-continued

<210> SEQ ID NO 10
<211> LENGTH: 30
<212> TYPE: DNA
<213> ORGANISM: Mus sp.

<400> SEQUENCE: 10
gcagggtttc acaaacttct cacatcttag 30

<210> SEQ ID NO 11
<211> LENGTH: 20
<212> TYPE: DNA
<213> ORGANISM: Mus sp.

<400> SEQUENCE: 11
cgcttcgccg cgtcaacccg 20

<210> SEQ ID NO 12
<211> LENGTH: 20
<212> TYPE: DNA
<213> ORGANISM: Mus sp.

<400> SEQUENCE: 12
cgcgtctgtc ccttgctcgg 20

<210> SEQ ID NO 13
<211> LENGTH: 30
<212> TYPE: DNA
<213> ORGANISM: Mus sp.

<400> SEQUENCE: 13
cctagtcatt ggtagcactg cagttactag 30

<210> SEQ ID NO 14
<211> LENGTH: 30
<212> TYPE: DNA
<213> ORGANISM: Mus sp.

<400> SEQUENCE: 14
agagcggtgg caatggcaat gacagtgaag 30

<210> SEQ ID NO 15
<211> LENGTH: 30
<212> TYPE: DNA
<213> ORGANISM: Mus sp.

<400> SEQUENCE: 15
gcgcaagagc gcgcagcatc ttcattgagg 30

<210> SEQ ID NO 16
<211> LENGTH: 30
<212> TYPE: DNA
<213> ORGANISM: Mus sp.

<400> SEQUENCE: 16
caccaagatg acagtgacag ataactgcag 30

<210> SEQ ID NO 17
<211> LENGTH: 30
<212> TYPE: DNA
<213> ORGANISM: Mus sp.

<400> SEQUENCE: 17

-continued

```
gcgaacatgg agttccatgt gcgtcttatg                                      30


<210> SEQ ID NO 18
<211> LENGTH: 30
<212> TYPE: DNA
<213> ORGANISM: Mus sp.

<400> SEQUENCE: 18

agtccctggc tttcttagat tccaacaacg                                      30


<210> SEQ ID NO 19
<211> LENGTH: 30
<212> TYPE: DNA
<213> ORGANISM: Homo sapiens

<400> SEQUENCE: 19

gccggacgca ccttcacttt gtggcaaatg                                      30


<210> SEQ ID NO 20
<211> LENGTH: 30
<212> TYPE: DNA
<213> ORGANISM: Homo sapiens

<400> SEQUENCE: 20

agcactgata atcaacaccc ggcctgtggg                                      30


<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: an adaptor
      sequence of an oligo cap

<400> SEQUENCE: 21

agcatcgagt cggccttgtt ggcctactgg                                      30


<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: the
      sequence of the 1st to 21st bases in the base
      sequence of SEQ ID NO: 21

<400> SEQUENCE: 22

agcatcgagt cggccttgtt g                                               21


<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: the
      sequence of the 11th to 30th bases in the base
      sequence of SEQ ID NO: 21

<400> SEQUENCE: 23

cggccttgtt ggcctactgg                                                 20


<210> SEQ ID NO 24
<211> LENGTH: 21
<212> TYPE: DNA
<213> ORGANISM: Mus sp.
```

-continued

<400> SEQUENCE: 24
tgcgtcagct ttggcagact g 21

<210> SEQ ID NO 25
<211> LENGTH: 22
<212> TYPE: DNA
<213> ORGANISM: Mus sp.

<400> SEQUENCE: 25
tctgtcatca tgagtctgaa gg 22

<210> SEQ ID NO 26
<211> LENGTH: 20
<212> TYPE: DNA
<213> ORGANISM: Mus sp.

<400> SEQUENCE: 26
cattgtcgtc gcagtcactg 20

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: the sequence of the 410th to 432nd bases in cloning vector pGL3-b (GenBank U47295)

<400> SEQUENCE: 27
tttataatga acgtgaattg ctc 23

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: the sequence complementary to the sequence of the 980th to 1000th bases in cloning vector pGL3-b (GenBank U47295)

<400> SEQUENCE: 28
cgtatttgtc aatcagagtg c 21

<210> SEQ ID NO 29
<211> LENGTH: 28
<212> TYPE: DNA
<213> ORGANISM: Homo sapiens

<400> SEQUENCE: 29
tccttacaag cagggatgca gtgagatg 28

<210> SEQ ID NO 30
<211> LENGTH: 28
<212> TYPE: DNA
<213> ORGANISM: Homo sapiens

<400> SEQUENCE: 30
aggcaaaggg gcgaacatta gagggtct 28

<210> SEQ ID NO 31
<211> LENGTH: 22
<212> TYPE: DNA
<213> ORGANISM: Homo sapiens -continued

```
<400> SEQUENCE: 31

tcttgtctgc agggaggtgg ac                                              22


<210> SEQ ID NO 32
<211> LENGTH: 22
<212> TYPE: DNA
<213> ORGANISM: Homo sapiens

<400> SEQUENCE: 32

aaattccgcg tatccattca tg                                              22
```

What is claimed is:

1. An isolated DNA which maintains a basal promoter activity and has a promoter activity transcriptionally-activated by a BMAL1/CLOCK heterodimer, which comprises the nucleotide sequence described in the following (a), (b), (c) or (d):

(a) a sequence consisting of nucleotides at positions 7,463 to 7,931 in the nucleotide sequence represented by SEQ ID NO:1, (b) a sequence consisting of nucleotides at positions 6,417 to 7,931 in the nucleotide sequence represented by SEQ ID NO:1, (c) a sequence consisting of nucleotides at positions 5,249 to 7,931 in the nucleotide sequence represented by SEQ ID NO:1, and (d) a sequence consisting of nucleotides at positions 4,415 to 7,931 in the nucleotide sequence represented by SEQ ID NO:1.

2. A DNA according to claim 1, which consists of the nucleotide sequence described in (a), (b), (c) or (d).

3. A construct which comprises the DNA according to claim 1 or 2 operably linked to a reporter gene.

4. A cell which comprises the construct according to claim 3.

5. A method for screening a substance which controls expression of Period2 gene, comprising the steps of:

allowing the cell according to claim 4 to contact with a substance to be tested, and measuring activity of the reporter gene.

6. A transgenic rat or mouse transfected with the construct according to claim 3, and wherein the suprachiasmatic nucleus and/or peripheral tissues of the rat or mouse exhibit the function of reporter gene expression.

7. The transgenic rat according to claim 6.

8. A method for screening a substance which controls expression and/or oscillatory expression of Period2 gene, comprising the steps of:

allowing the cell according to claim 4 to react with a substance to be tested, and measuring activity of the reporter gene for oscillatory expression of the Period2 gene.

9. A method for screening a substance which controls expression and/or oscillatory expression of Period2 gene, comprising the steps of:

administering a substance to be tested to the transgenic rat or mouse according to claim 6, and measuring activity of the reporter gene in the suprachiasmatic nucleus of the animal for oscillatory expression of the Period2 gene.

10. A method for screening a substance which controls expression and/or oscillatory expression of Period2 gene, comprising the steps of:

allowing a suprachiasmatic nucleus section or peripheral tissue of the transgenic rat or mouse according to claim 6 to react with a substance to be tested, and measuring activity of the reporter gene for oscillatory expression of the Period2 gene.

11. The transgenic rat or mouse according to claim 6, wherein the reporter gene is one member selected from the group consisting of a gene encoding luciferase, a gene encoding secretion type alkaline phosphatase (SEAP), a gene encoding green fluorescent protein (GFP), a gene encoding chloramphenicol acetyltransferase (CAT), a gene encoding β-glucuronidase (GUS), a gene encoding β-D-galactosidase and a gene encoding aequorin.

12. The transgenic rat according to claim 7, wherein the reporter gene is one member selected from the group consisting of a gene encoding luciferase, a gene encoding secretion type alkaline phosphatase (SEAP), a gene encoding green fluorescent protein (GFP), a gene encoding chloramphenicol acetyltransferase (CAT), a gene encoding β-glucuronidase (GUS), a gene encoding β-D-galactosidase and a gene encoding aequorin.

* * * * *